United States Patent
Zhang et al.

(10) Patent No.: US 9,439,621 B2
(45) Date of Patent: Sep. 13, 2016

(54) REDUCED IMAGE READING TIME AND IMPROVED PATIENT FLOW IN AUTOMATED BREAST ULTRASOUND USING ENCHANCED, WHOLE BREAST NAVIGATOR OVERVIEW IMAGES

(71) Applicants: Wei Zhang, San Jose, CA (US); Shih-Ping Wang, Los Altos, CA (US); Alexander Schneider, Los Altos, CA (US); Harlan Romsdahl, Half Moon Bay, CA (US); Thomas Neff, Newark, CA (US)

(72) Inventors: Wei Zhang, San Jose, CA (US); Shih-Ping Wang, Los Altos, CA (US); Alexander Schneider, Los Altos, CA (US); Harlan Romsdahl, Half Moon Bay, CA (US); Thomas Neff, Newark, CA (US)

(73) Assignee: QVIEW, MEDICAL INC, Los Altos, CA (US)

(*) Notice: Subject to any disclaimer, the term of this patent is extended or adjusted under 35 U.S.C. 154(b) by 0 days.

(21) Appl. No.: 14/448,607

(22) Filed: Jul. 31, 2014

(65) Prior Publication Data

US 2014/0343420 A1 Nov. 20, 2014

Related U.S. Application Data

(63) Continuation-in-part of application No. 12/839,371, filed on Jul. 19, 2010, and a continuation-in-part of application No. PCT/US2014/048897, filed on Jul. 30, 2014, and a continuation-in-part of application No.

(Continued)

(51) Int. Cl.
*A61B 8/08* (2006.01)
*A61B 8/00* (2006.01)

(Continued)

(52) U.S. Cl.
CPC ............ *A61B 8/0825* (2013.01); *A61B 8/13* (2013.01); *A61B 8/403* (2013.01); *A61B 8/469* (2013.01);

(Continued)

(58) Field of Classification Search
CPC .............. G06T 7/0081; G06T 2207/30068; A61B 8/463; A61B 6/12
USPC ......... 382/132, 128, 131; 600/408, 437, 300
See application file for complete search history.

(56) References Cited

U.S. PATENT DOCUMENTS 6,317,617 B1* 11/2001 Gilhuijs et al. ............... 600/408
6,876,879 B2* 4/2005 Dines ................... A61B 6/0414
128/915

(Continued)

FOREIGN PATENT DOCUMENTS

WO WO2015017542 2/2015
WO WO2015084681 6/2015

OTHER PUBLICATIONS

Linda J. Warren Burhenne et al., Potential Contribution of Computer-aided Detection to the Sensitivity of Screening Mammography, Radiology 2000;vol. 215: 554-562.

(Continued)

*Primary Examiner* — Victoria P Shumate
*Assistant Examiner* — Teresa Williams
(74) *Attorney, Agent, or Firm* — Cooper & Dunham LLP

(57) ABSTRACT

A method and system acquiring, processing and displaying breast ultrasound images in a way that makes breast ultrasound screening more practical and thus more widely used, and reduces missing cancers in screening and diagnosis, using automated scanning of chestwardly compressed breasts with ultrasound. Enhanced, whole-breast navigator overview images are generated from scanning breasts with ultrasound that emphasize abnormalities in the breast while excluding obscuring influences of non-breast structures, particularly those external to the breast such as ribs and chest wall, and differentiating between likely malignant and likely benign abnormalities and otherwise enhancing the navigator overview image and other images, to thereby reduce the time to read, screen, or diagnose to practical time limits and also reduce screening or diagnostic errors.

22 Claims, 33 Drawing Sheets

Related U.S. Application Data

13/512,164, filed on Nov. 9, 2012, and a continuation-in-part of application No. 14/044,842, filed on Oct. 2, 2013, and a continuation-in-part of application No. 14/084,589, filed on Nov. 19, 2013, and a continuation-in-part of application No. PCT/US2009/066020, filed on Nov. 27, 2009.

(60) Provisional application No. 61/860,900, filed on Jul. 31, 2013, provisional application No. 61/910,139, filed on Nov. 29, 2013, provisional application No. 62/003,448, filed on May 27, 2014.

(51) Int. Cl.
  *A61B 8/13* (2006.01)
  *G06T 7/00* (2006.01)

(52) U.S. Cl.
  CPC ........... *A61B 8/5215* (2013.01); *G06T 7/0012* (2013.01); *G06T 2207/10132* (2013.01); *G06T 2207/30068* (2013.01)

(56) References Cited

U.S. PATENT DOCUMENTS

| | | | | |
|---|---|---|---|---|
| 6,909,794 | B2* | 6/2005 | Caspi | G06T 3/0068 382/128 |
| 7,426,290 | B1* | 9/2008 | Khan et al. | 382/132 |
| 7,615,008 | B2* | 11/2009 | Zhang et al. | 600/437 |
| 7,699,783 | B2* | 4/2010 | Hanover et al. | 600/459 |
| 8,194,947 | B2* | 6/2012 | Zingaretti | G06T 7/0012 382/128 |
| 8,473,538 | B2* | 6/2013 | Beckman | G06F 7/548 708/442 |
| 8,576,911 | B2 | 11/2013 | Seong | |
| 8,977,052 | B2 | 3/2015 | Seong | |
| 9,025,858 | B2 | 5/2015 | Seong | |
| 9,084,578 | B2 | 7/2015 | Seong | |
| 9,202,279 | B2 | 12/2015 | Seong | |
| 9,305,349 | B2 | 4/2016 | Seong | |
| 9,361,685 | B2 | 6/2016 | Seong | |
| 2001/0033680 | A1* | 10/2001 | Bankman et al. | 382/128 |
| 2005/0152588 | A1* | 7/2005 | Yoshida et al. | 382/128 |
| 2006/0251301 | A1* | 11/2006 | McNamara | A61B 6/0435 382/128 |
| 2007/0206844 | A1* | 9/2007 | Russakoff et al. | 382/132 |
| 2008/0085057 | A1* | 4/2008 | Ratner et al. | 382/242 |
| 2008/0208048 | A1* | 8/2008 | Maruyama | A61B 8/06 600/437 |
| 2009/0080765 | A1* | 3/2009 | Bernard | G06T 11/006 382/128 |
| 2012/0189178 | A1 | 7/2012 | Seong | |
| 2013/0022253 | A1 | 1/2013 | Seong | |
| 2013/0030278 | A1 | 1/2013 | Seong | |
| 2013/0094766 | A1 | 4/2013 | Seong | |
| 2013/0114904 | A1 | 5/2013 | Seong | |
| 2013/0116535 | A1 | 5/2013 | Seong | |
| 2013/0245426 | A1 | 9/2013 | Seong | |
| 2014/0037159 | A1 | 2/2014 | Seong | |
| 2014/0039318 | A1 | 2/2014 | Zhang et al. | |
| 2014/0101080 | A1 | 4/2014 | Seong | |
| 2014/0105473 | A1 | 4/2014 | Seong | |
| 2014/0105474 | A1 | 4/2014 | Seong | |
| 2014/0122515 | A1 | 5/2014 | Seong | |
| 2014/0142413 | A1 | 5/2014 | Seong | |
| 2014/0153807 | A1 | 6/2014 | Seong | |
| 2014/0185900 | A1 | 7/2014 | Seong | |
| 2014/0193051 | A1 | 7/2014 | Seong | |
| 2014/0194722 | A1 | 7/2014 | Seong | |
| 2014/0200452 | A1 | 7/2014 | Seong | |
| 2014/0228687 | A1 | 8/2014 | Seong | |
| 2014/0241606 | A1 | 8/2014 | Seong | |
| 2015/0003677 | A1 | 1/2015 | Seong | |
| 2015/0087979 | A1 | 3/2015 | Zhang et al. | |
| 2015/0146958 | A1 | 5/2015 | Seong | |
| 2015/0157298 | A1 | 6/2015 | Seong | |
| 2015/0173705 | A1 | 6/2015 | Seong | |
| 2015/0187071 | A1 | 7/2015 | Seong | |
| 2015/0230773 | A1 | 8/2015 | Seong | |
| 2015/0254846 | A1 | 9/2015 | Seong | |
| 2015/0265251 | A1 | 9/2015 | Seong | |
| 2015/0302583 | A1 | 10/2015 | Seong | |
| 2015/0317794 | A1 | 11/2015 | Seong | |
| 2015/0339859 | A1 | 11/2015 | Seong | |
| 2016/0019320 | A1 | 1/2016 | Seong | |
| 2016/0019441 | A1 | 1/2016 | Seong | |
| 2016/0042525 | A1 | 2/2016 | Seong | |
| 2016/0171299 | A1 | 6/2016 | Seong | |

OTHER PUBLICATIONS

Karen Drukker et al., Computerized lesion detection on breast ultrasound, Medical Physics 29 (7), Jul. 2002.

Karen Drukker et al., Computerized detection of breast cancer on automated breast ultrasound imaging of women with dense breasts, Medical Physics 41, 012901 (2014).

Woo Kyung, Moon et al. Computer-aided classification of breast masses using speckle features of automated breast ultrasound images,Medical Physics 39, 6465 (2012).

Vijay M. Roa, MD et al., How Widely Is Computer-aided Detection used in Screening and Diagnostic Mammography? 2010 American College of Radiology p. 802-805.

Tao Tan et al., Computer-Aided Detection of Cancer in Automated 3-D Breast Ultrasound. IEEE Transactions on Medical Imaging vol. 32 No. 9 Sep. 2013 p. 1698-1706.

Tao Tan et al., Computer-Aided Lesion Diagnosis in Automated 3-D Breast Ultrasound Using Coronal Spiculation IEEE Transactions on Medical Imaging vol. 31, No. 5, 5/12 p. 1034-42.

* cited by examiner

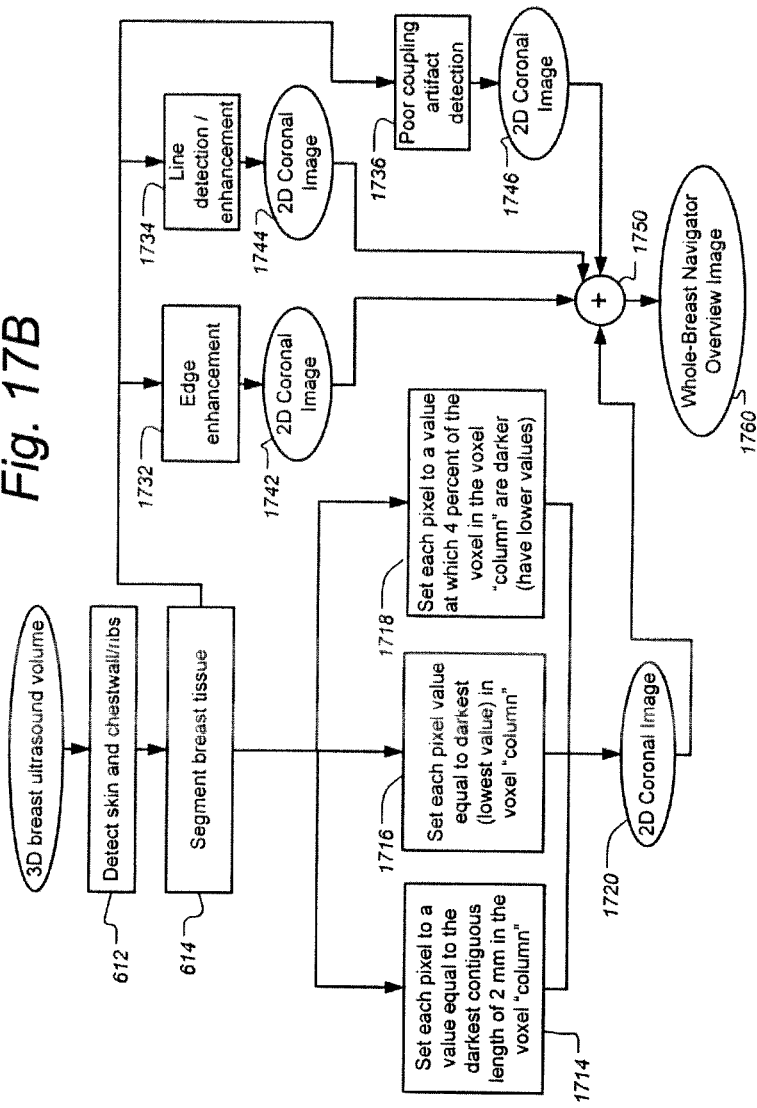

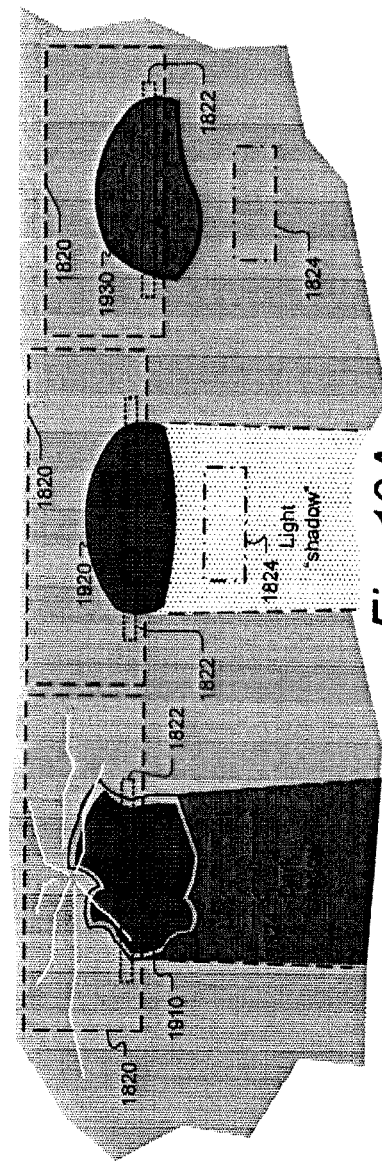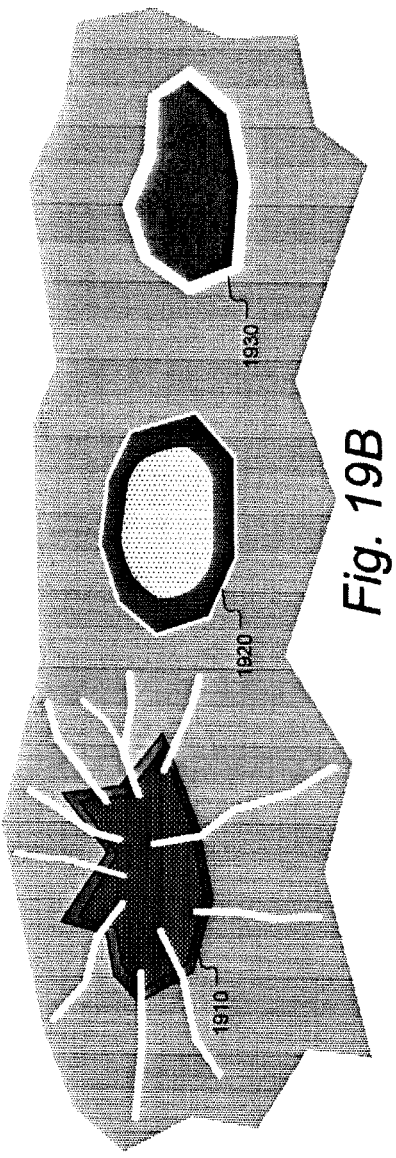

REDUCED IMAGE READING TIME AND IMPROVED PATIENT FLOW IN AUTOMATED BREAST ULTRASOUND USING ENCHANCED, WHOLE BREAST NAVIGATOR OVERVIEW IMAGES

REFERENCE TO RELATED APPLICATIONS

This patent application claims the benefit of and incorporates by reference each of the following applications:
 U.S. Prov. Ser. No. 61/860,900 filed on Jul. 31, 2013;
 U.S. Prov. Ser. No. 61/910,139 filed on Nov. 29, 2013; and
 U.S. Prov. Ser. No. 62/003,448 filed on May 27, 2014.

This application is a continuation-in-part of and incorporates by reference each of the following applications:
 International Patent Application No. WO 2011/065950 A1 filed on Nov. 27, 2009;
 U.S. Ser. No. 12/839,371 filed on Jul. 19, 2010, published on Jan. 19, 2012 as U.S. Publ. No. 2012/0014578;
 U.S. Ser. No. 13/512,164 filed on Nov. 9, 2012, published on Feb. 28, 2013 as U.S. Publ. No. 2013/0050239;
 U.S. Ser. No. 14/044,842 filed on Oct. 2, 2013, published on Feb. 6, 2014 as U.S. Publ. No. 2014/0039318; and
 U.S. Ser. No. 14/084,589 filed on Nov. 19, 2013, published on Mar. 20, 2014 as U.S Publ. No. 2014/0082542; and
 International Application No. PCT/US14/48897, filed on Jul. 30, 2014.

FIELD

The methods and systems described in this patent specification relate to the field of early detection of breast cancer using ultrasound. More specifically, the methods and systems described in this patent specification relate to acquiring, enhancing, and displaying breast ultrasound images and other information in a manner believed to improve patient screening and diagnosis. Even more specifically, the patent specification relates to methods and systems of reducing the time for assessing patients for breast abnormalities and improving patient flow for ultrasound breast examination related to acquiring sonographic responses from patient tissue and generating and displaying enhanced, whole-breast navigator overview images that are particularly efficacious both in identifying likely abnormalities and their nature and in enhancing workflow. A goal is to reduce the time to assess the beast for abnormalities and reduce error in assessment and make breast cancer detection with ultrasound more practical and thus more widely used, to thereby help women by early detection and accurate screening or diagnosis, particularly women with breasts that are relatively dense to x-rays and therefore may not be screened or diagnosed as effectively with standard x-ray mammograms.

BACKGROUND

In the US, the expected statistical figures for breast cancer in 2013 are estimated at approximately 230,000 new cases and 40,000 deaths. The mortality rate can be lowered if breast cancer could be detected in an earlier stage. Screening with X-ray mammography has been the gold standard for the early detection of breast cancer. However, in about 40% of the screening population the women typically more than 50% of their breasts made up of dense fibro-glandular breast tissues that tend to obscure abnormalities in X-ray mammograms. Recent clinical studies show that this "dense breast" gap could be economically and sufficiently dealt with using breast ultrasound, particularly automated three-dimension ("3D") breast ultrasound. Currently, the only breast ultrasound system that received USFDA approval for breast cancer screening is an automated 3D breast ultrasound system using a chestward compression scanning procedure.

There are two major challenges facing any practical breast cancer screening modality. The first challenge is cost, which can be measured as the cost of the actual examination and assessment of the results, and as the cost per detected cancer. Since breast cancer has a very low prevalence rate such that one cancer is generally found in 200 to 300 asymptomatic patients screened, the per patient screening cost must be kept low, currently typically to the range of $100-$200 in the U.S., in order to achieve a reasonable cost per cancer detected (i.e. $20,000 to $60,000 range). This cost range is generally translated into limiting typical reading/interpretation time to about 3 minutes per patient, using an automated scanning system with a throughput of over 2,000 patients per year. For screening X-ray mammography, where only 4 new images are generated per patient at a screening examination in U.S. practice, this 3-minute interpretation time requirement is relatively easily met. However, for current commercial breast ultrasound screening examinations, where over 1,000 new two-dimensional ("2D") images obtained by scanning in substantially axial direction under chestward compression (often called "original" images) are typically generated per patient, the 3 minutes of reading/interpretation time limit is very difficult to meet. An associated rapid reading method is used by configuring the original axial images first into coronal thin-slice images and then into composite coronal thick-slice images, e.g., 2-30 coronal thin-slice images into one thick-slice image, so that a user can better search for abnormalities and better manage the reading/interpretation time. See for example U.S. Pat. No. 7,828,733, where the coronal thick-slices method is discussed. However, this method is still not quite fast enough, nor could it satisfactorily solve the "oversight" challenge described immediately below.

The second major challenge of breast cancer screening is the oversight, where obvious cancers are overlooked. A delay in cancer detection due to oversight can cause the cancer to progress to a more advanced stage resulting in decreased patient survivability and increased treatment cost. This problem is particularly serious when trying to read/interpret breast images quickly. A study on blind re-reading of 427 prior screening x-ray mammograms, which were taken a year before the cancer detection, published in Radiology (by Warren-Burhenne et al., 2000, Vol. 215, pages 554-562), reports that as many as 115 (or 27%) of the cancers could have been detected a year earlier and should be classed as oversights. In order to reduce the oversight problem, commercial computer-aided diagnosis ("CAD") systems have been developed for X-ray mammography screening. Development of clinically useful x-ray mammography CAD was no trivial matter, as the CAD must achieve sensitivities close to that of human readers. The development was undertaken by several commercial firms, some in collaboration with universities and national laboratories, over many years, and is believed to have consumed over $100 million in combined developmental cost. The CAD's impact is clearly visible—after 10 years of its commercial introduction, as reported by a study published in JACR (by Rao et al., 2010, Vol. 7, pages 802-805) by year 2008, 75% of the screening x-ray mammograms were read with CAD assistance.

In the known commercial automated 3D breast ultrasound systems, the ultrasound beam is generally directed chestwardly during the scan while the breast is generally compressed chestwardly. This method has many advantages over the earlier non-chestward-compressed ultrasound scanning method proposals, such as a method that clamps the breast between vise-like scanning plates, as in standard x-ray mammography. The advantages of chestward scanning include: improved patient comfort, thinner breast tissue slices imaged during the scan, and the possibility of employing higher ultrasound frequency resulting in greater image quality. This is discussed in more detail in U.S. Pat. No. 7,828,733. A composite coronal thick-slice method (2-20 mm in slice thickness), which could be used as a guide or road map to aid the search for abnormalities, is also discussed in U.S. Pat. No. 7,828,733, as is the possibility of a full-breast composite image 2502 that preferably is a CAD enhanced expression of the sonographic properties of substantially the entire breast volume, i.e., all of the tissue imaged by the volumetric ultrasound scans, and of enhancing lesions according to their likelihood of malignancy (or other metric of interest). The thick-slice coronal image has been proven helpful as a road map in current commercial automated 3D breast ultrasound systems. In commercial systems, a popular slice thickness of the coronal thick slice is believed to be 2 mm, which is selected for reasons of good image quality and less chance to miss smaller lesions or abnormalities. Slice thickness down to 0.5 mm also is believed to be used.

In commercial automated 3D breast ultrasound screening systems using chestward compression scans, for each patient, several scans are typically made on each breast, for example 2-5 scans, although in some cases it can be a single scan and in some cases more than 5 scans. Each typical scan generates about 300 new images. Thus, 1,200 to 2,400 or more new images can be generated for each patient. With the manifold, e.g., 300 to 600-fold increase in the number of new images over screening x-ray mammography, readers can encounter even more oversights than the 27% or so that can be encountered in screening x-ray mammography. Thus, efficient methods and systems should be developed to better manage both the reading/interpretation time as well as the oversight problems before breast ultrasound screening could be more broadly employed to help more women. Since the worldwide commercial introduction of automated 3D breast ultrasound using chestward compression several years ago, radiologists at hundreds of facilities around the world have been struggling to read/interpret the huge volume of breast ultrasound images per patient study. At the present time, it is believed that only the best readers, even using the composite 2 mm coronal thick-slice image as road maps, are able reach the 3 minutes practical limit per patient, while the majority of the readers are averaging more than 5 to 8 minutes per patient. No published studies on the "oversight" in current commercial automated 3D breast ultrasound are known, but one could venture to guess that the oversight rate could not have been below that found for screening mammography, i.e., more than the reported 27%.

The subject matter claimed herein or in a patent issuing from this patent specification is not limited to embodiments that solve any particular disadvantages or that operate only in environments such as those described above. Rather, this background is only provided to illustrate one exemplary technology area where some embodiments described herein may be practiced.

All the publications, including patents, cited throughout this patent specification, are hereby incorporated by reference.

SUMMARY

Some of the embodiments described in this patent specification relate to systems and methods for automated ultrasound examination of a patient's breast in which: a breast scanning pod compresses the patient's breast chestwardly and scans the compressed breast with ultrasound to acquire a sonographic response; a processor applies computer image processing to the sonographic response to produce an enhanced whole-breast navigator overview image representing a three-dimensional volume from which influences of non-breast tissue included in the sonographic response has been segmented out. The processor further enhances the whole-breast navigator overview image with indications of abnormalities found in the sonographic response, indications of whether the found abnormalities are likely malignant or likely benign, and boosted representations of features related to likely malignant abnormalities; and a computerized display shows the enhanced, whole-breast navigator overview image, typically in association with selected other images generated from the sonographic response.

The non-breast tissue whose influence is segmented out can include one or more of ribs, pectoral muscle, and skin or skin plus a thin underlying layer of tissue that may be unavoidably included in the sonographic response. The indications of abnormalities can be generated mainly by applying one or more computer-aided detection (CAD) algorithms to the sonographic response or images derived from the sonographic response, or mainly by image processing that highlights image areas of likely abnormalities. Influences of artifacts in the whole-breast navigator overview image can be detected and the appearance of the detected artifacts diminished in the displayed navigator overview images. Representations in the enhanced, whole-breast navigator overview image of features related to likely malignant abnormalities, such as spiculations, can be boosted by making the features darker or lighter than if not boosted. The image of a detected cyst can be enhanced in the displayed navigator overview image by placing a spot therein that differs from a remainder of the cyst image. Other detected abnormalities can be made more prominent in the image by various image changes. Influences of sonographic response content resulting from poor ultrasound transducer-to-breast coupling can be detected and diminished in the displayed enhanced, whole-breast navigator overview image. The whole-breast navigator overview image can be obtained through a process that includes assigning to a pixel in the navigator overview image a value related to the darkest voxel value in a related column of voxels in the three-dimensional breast volume, or a value related to voxel values along a stretch such as a stretch of 1-3 mm containing the darkest voxel values of a related column of voxels rather than all the voxel values in the column, or more generally a value controlled by only some of the voxel values of a related column of voxels, or a value controlled by one or more voxel values of a related column of voxels in the three-dimensional volume that have a darkness or lightness value meeting a selected threshold of darkness or lightness.

Some embodiments relate to systems and methods for automated ultrasound examination of a patient's breast in which: a breast scanning pod compresses the patient's breast chestwardly and scans the compressed breast with ultrasound to acquire a sonographic response; a processor applies computer image processing to the sonographic response to thereby produce a whole-breast navigator overview image representing a three-dimensional breast volume and segments out influences of non-breast tissue interactions with ultrasound in said scanning to thereby produce an enhanced, whole-breast navigator overview image; and a computerized display shows the enhanced, whole-breast navigator overview image, typically in association with selected other images generated from the sonographic response. The breast scanning pod can carry out multiple scans of a breast and/or can acquire sonographic responses from both breasts of the patient, the processor can obtain plural enhanced, whole-breast navigator overview images related to the respective plural scans of the patient's breasts, and the display can concurrently display the plural enhanced, whole-breast navigator overview images. The processor can form reduced-size images of the enhanced, whole-breast navigator overview images, and the display can concurrently show the reduced size images plus at least one full-size version of a reduced-size image, or at least one full-size version for each of the two breasts. The displayed full-size enhanced, whole-breast navigator overview images for each of the patient's breasts can be for matching orientation scans of the breasts with the pod. Bookmarks can be acquired and stored regarding breast abnormalities that a user has viewed, and can include information regarding characteristics of the respective bookmarked abnormalities. The display can automatically include a concurrent display of one or more thick-slice images that shows a selected abnormality found in the enhanced, whole-breast navigator overview image, at least one image of a region of interest in the original thin-slice image that includes an abnormality selected in the enhanced, whole-breast navigator overview image, who such images of ROIs such as in orthogonal orientation, and/or thin-slice images in one or more orientations such as in the orientation of an original thin-slice and of a synthesized thin-slice in an orthogonal orientation.

Some embodiments relate to systems and methods for automated ultrasound examination of a patient's breast in which: a breast scanning pod compresses the patient's breast chestwardly and scans the compressed breast with ultrasound to acquire a sonographic response; a processor applies computer image processing to the sonographic response to thereby produce an enhanced, whole-breast navigator overview image representing a three-dimensional volume and representations of abnormalities found in the breast as wells as indications that differentiate between likely malignant and likely benign abnormalities found in the breast; and a computerized display shows the enhanced, whole-breast navigator overview image with such indications, typically and in association with selected other images generated from the sonographic response.

Some embodiments relate to systems and methods for automated ultrasound examination of a patients breast in which: a breast scanning pod compresses the patient's left and a right breast chestwardly and scans the compressed breasts with ultrasound to acquire a sonographic response from each of the breasts; a processor applies computer image processing to the sonographic responses from the two breasts to thereby produce, for each of the breasts, at least one enhanced, whole-breast navigator overview image representing a three-dimensional volume of the breast and including representations of abnormalities found in the breast; and a computerized display concurrently shows at least one enhanced, whole-breast navigator overview image for each of the two breasts, or at least one pair of such navigator overview images containing an image of each breast.

At least some of the described embodiments include equipment for scanning the breast with ultrasound and receiving a sonographic response but it should be understood that the desired enhanced, whole-breast navigator overview images can be obtained in equipment such as workstations that receive and process sonographic responses or related images from sources such as PACS or through a wired or wireless link with facilities that separate the workstation from the sonographic response or initial image processing or storage facilities.

It will be appreciated that these systems and methods are novel, as are applications thereof and many of the components, systems, methods and algorithms employed and included therein. It should be appreciated that embodiments of the presently described inventive body of work can be implemented in numerous ways, including as processes, apparata, systems, devices, methods, computer readable media, computational algorithms, embedded or distributed software and/or as a combination thereof. Several illustrative embodiments are described below.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments, and are therefore not to be considered limiting of the scope of this patent specification or the appended claims. The subject matter hereof will be described and explained with additional specificity and detail through the use of the accompanying drawings in which:

FIG. 17B is a flow chart illustrating aspects of generating an enhanced, whole-breast navigator overview image based on 3-D image data without using CAD, according to some embodiments;

FIGS. 19A and 19B are transversal and coronal views, respectively, illustrating CAD ROI alteration techniques, according to some embodiments;

DETAILED DESCRIPTION

Figure 1A:
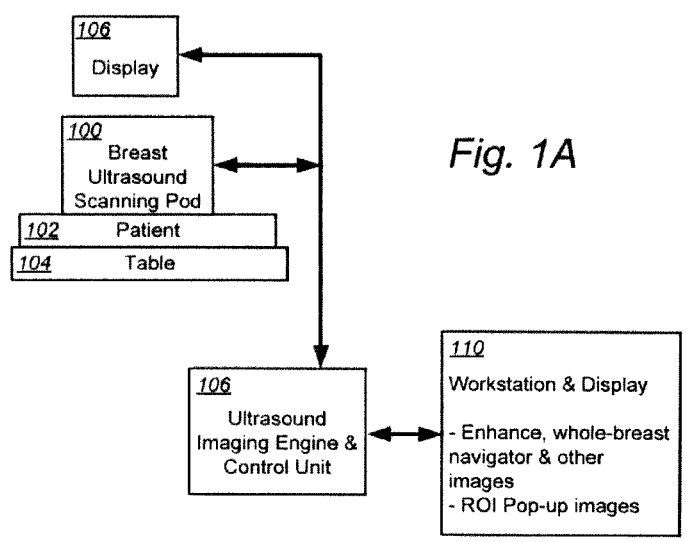
FIG. 1A illustrates aspects of new features disclosed in this patent specification when incorporated in a known commercial system for automated scanning of a patient's breast with ultrasound.

A detailed description of examples of embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

According to some embodiments, one or more ultrasound transducers transmit ultrasound energy into a patient's breast and receive sonographic responses that are converted through processing in computer circuits into a three-dimensional (3D) representation of tissue producing the responses, which 3D representation is enhanced by removing influences of non-breast tissue and from which are derived one or more enhanced, whole-breast navigator overview images that are uniquely configured to speed up the screening and diagnosis of the patient's breast and to reduce occurrences of missed lesions. The navigator overview images can be further configured to include indications, such as computer-aided detection (CAD) marks or enhancements that rely mainly on other processes, that identify as such both likely malignant and likely benign abnormalities found in the breast, and to enhance the representation of certain aspects of abnormalities, and can be displayed together with other images that can help further characterize the abnormalities.

According to some embodiments, interactive user interface methods and systems are described that can shorten the time to view and assess important breast ultrasound images within a time limit of approximately 3 minutes and with low oversight.

According to some embodiments, a novel CAD-driven navigator overview image display method and system are disclosed. The navigator overview image is configured to assist the readers to reduce their reading/interpretation time and at the same time to provide comfort and confidence such that oversights would be reduced.

According to some embodiments, the display method and system show to the readers the abnormalities in a navigator overview image derived from 3D volumetric scans, where the abnormalities were image processed, with little or no traditional CAD involved, by displaying at each pixel location a combined, e.g., a low average, value selected from a set of voxels in a voxel column that can be oriented in the chestward direction. According to some other embodiments, the navigator overview image is more CAD driven, where CAD is employed to detect and enhance the displayed abnormalities. According to yet other embodiments, CAD is employed to detect both malignant-looking abnormalities as well as benign-looking abnormalities. The navigator overview image displays additional features, showing both malignant and benign characteristics in a way to classify these abnormalities, to enable the readers to place higher priority on viewing the more suspicious abnormalities. Thus, this would further reduce the reading/interpretation time. CAD is important in detecting and thus reducing obvious oversights. CAD marks or CAD probability figures can be displayed anytime (before, during or after readers looked the navigator overview image) at the readers preference or as preset for the equipment.

According to some embodiments, a method and system for processing and displaying breast ultrasound information are provided, wherein a feature weighted volumetric navigator overview image is generated from the 3D ultrasound data volume to represent the 3D dataset with the goal of emphasizing abnormalities found within the breast while excluding some or all non-breast tissue or structures, particularly those external to the breast such as ribs and chest wall, and optionally skin and immediately adjacent tissue, in accordance with the method and system described herein.

According to some embodiments, the navigator overview image is displayed in addition to and together with a display of images available in current commercial automated 3D breast ultrasound systems employing chestward compression scans, where a 2D original axial scan image, and a 2D orthogonal (constructed to be orthogonal to the axial scan) image are displayed with 2D coronal thick-slice images. By clicking any exhibited abnormality in the navigator overview image, with pre-calculated xyz coordinates, the corresponding abnormality can show up in the 2D coronal thick-slice image, as well as at the corresponding locations in the 2D original axial scan image and the orthogonal sagittal image.

According to some embodiments, the navigator overview image is displayed together with just the 2D original axial scan image for the quickest review and a snippet of one or more 2D images of coronal thick-slices. It is sometimes useful to show the coronal thick-slice image, because readers may like to confirm their assessment by examining the presence of spiculations of a mass nodule that only show, or show better, in composite coronal thick-slices. The quick review of the 2D axial scan images can be done in the manner described above.

According to some embodiments, the navigator overview image is displayed in inverted polarity. That is, in a regular display, the abnormalities are dark colored on relatively light breast tissue background, and in the inverted polarity, the abnormalities are light colored on a relatively dark breast tissue background. Some readers may find it more useful to read the inverted polarity guides, which resemble mammograms (also with lighter colored abnormalities such as calcifications on a darker background).

According to some embodiments, the navigator overview image is generated through a process of segmenting away non-breast structure and using a filter to enhance the remaining volumetric breast tissue to make the abnormalities more visible and more prominent.

According to some embodiments, the filter includes a computer aided detection (CAD) algorithm that detects and ranks the lesions by likelihood. This is particularly useful for very small abnormalities or lesions that show significant likelihood of being malignant by CAD, and yet the above described filter may not be enough to make these small abnormalities as visible or prominent in the navigator overview image.

According to some embodiments, additional information is shown with an abnormality such as its size, volume, relative probability, likelihood of being malignant, etc.

According to some embodiments, the navigator overview image is displayed on a separate monitor situated for convenient viewing, e.g., adjacent to the display monitor of a commercial automated 3D breast ultrasound system while in other embodiments all images are on the same screen, which also may show other information.

According to some embodiments, two or more navigator overview images are displayed, typically concurrently, each for a respective breast of the patient or for a respective scan of a breast with an ultrasound transducer, while in other embodiments different images can alternate or be superimposed, possibly with different degrees of transparency.

According to some embodiments, the navigator overview image is displayed on a separate sheet of paper to be viewed with the display monitor of a commercial automated 3D breast ultrasound system.

FIG. 1A illustrates aspects of a commercially available breast ultrasound imaging system that has been modified in accordance with this patent specification to generate and use whole-body navigator overview images. It can be a system such as discussed in U.S. Pat. Nos. 7,828,733 and 8,496,586 or an ABUS system currently offered commercially in the U.S. by GE Healthcare and previously available from U-Systems, Inc. of California. The system includes a breast scanning pod 100 which can be brought down to chestwardly compress a breast of a patient 102 resting supine on a table 104. Pod 100 includes a mechanically driven transducer that scans the compressed breast through a coupling medium to send ultrasound energy into the breast and receive a sonographic response. Ultrasound engine and control unit 106 interacts with pod 100 to control the scanning and generation of the sonographic response and to process the response into desired ultrasound images. The images and other information can be displayed on a monitor 108 that can be on a common support with pod 100 and, additionally can be supplied to a workstation 110 through a wired or wireless connection, directly or indirectly such as through a hospital's PACS facilities, for further processing and for display. According to some embodiments, information can be accessed from a server via a standard protocol such as DICOM. Further details of the basic system can be found in the cited patents or in information regarding the commercially available system but are not included here for the sake of conciseness. The system is modified to process the sonography response as described below, using the computing facilities of engine 106 and/or workstation 110 through the operation of algorithmic software, firmware, and/or hardware to carry out processing described below.

Figure 1B:
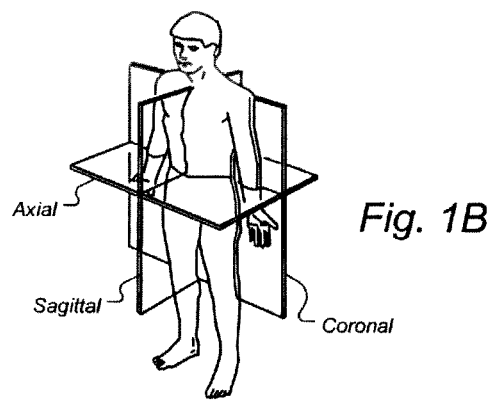
FIG. 1B illustrates a convention for image orientation used in this patent specification.

FIG. 1B illustrates convention for image orientation adopted in this patent specification. For breast images, a coronal slice is approximately parallel to a patient's chest wall, an axial slice extends left-right through the breast, and a sagittal slice extends head-to-foot across the breast.

Figure 2:
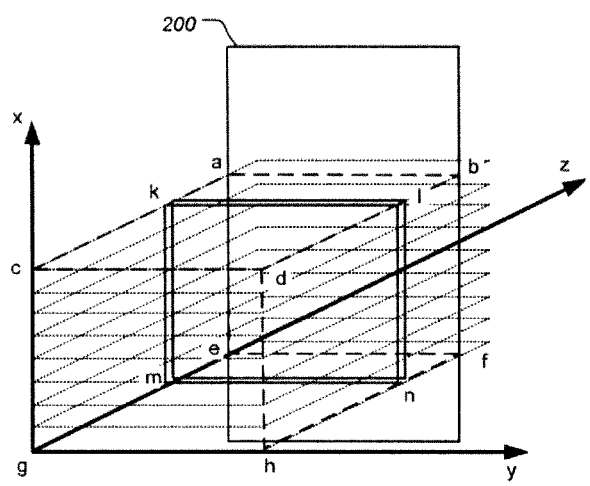
FIG. 2 illustrates aspects of chestward compression scan orientation in relationship to a thick-slice, as well as a volume from which a whole-breast navigator overview image can be derived, according to some embodiments.

FIG. 2 illustrates aspects of chestward compression scan orientation in relationship to a 2D coronal thick-slice of a patient's breast, as well as a volume from which an enhanced, whole-breast navigator overview image can be derived, according to some embodiments. Shown are a 2D coronal thick-slice guide (k,l,m,n), and the volume (a,b,c,d, e,f,g,h) from which the enhanced, whole-breast navigator overview image can be derived. Chestwall 200 is also shown. The planes a,b,c,d to e,f,g,h are original axial thin-slice scanned images. The z-direction in FIG. 2 is a chestward direction, and the axial images are in planes that are perpendicular to the length of the patient.

In this patent specification, the original axial scan images are sometimes referred to as thin-slice images because each represents a very thin slice of tissue, such as 0.1 mm or even less. The term thick-slice image refers to an image equivalent to a combination of several thin-slice images and typically representing a tissue slice that is 0.5-20 mm thick, although variations are possible. The term whole-breast navigator overview image refers to an image that represents a 3D volume of tissue that is substantially thicker than a thin-slice or a thick-slice, and can be the entire volume that generates the sonographic response used for images or at least a volume remaining after segmenting out influences of tissue that can obscure the portions of the breast of primary interest. Such influences can be content of the sonographic response due to the patient's ribs, chest wall (pectoral muscle(s) and connective tissue), and skin plus possibly a layer of breast tissue close to the skin, where malignancies can be expected to be found through means other than ultrasound imaging. The term user in this patent specification refers to the person who operates the system to generate the sonographic response from which the images are derived and/or a person who views or otherwise utilizes the images to screen and/or diagnose a breast or a patient.

Figure 3:
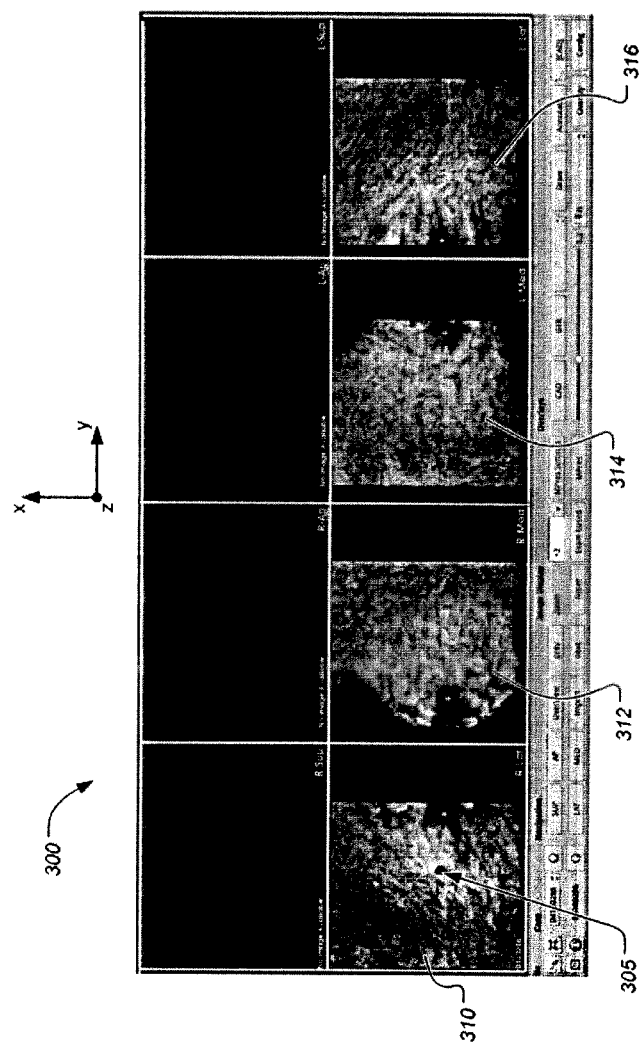
FIG. 3 illustrates aspects of a start-up screen with two enhanced, whole-breast navigator overview images from each of the patient's breasts: two from scanning a lateral portion of the right breast (R-Lat) and of the left breast (L-Lat) and two from scanning a medial portion of the right breast (R-Med) and of the left breast (L-Med), according to some embodiments.
Figure 4:
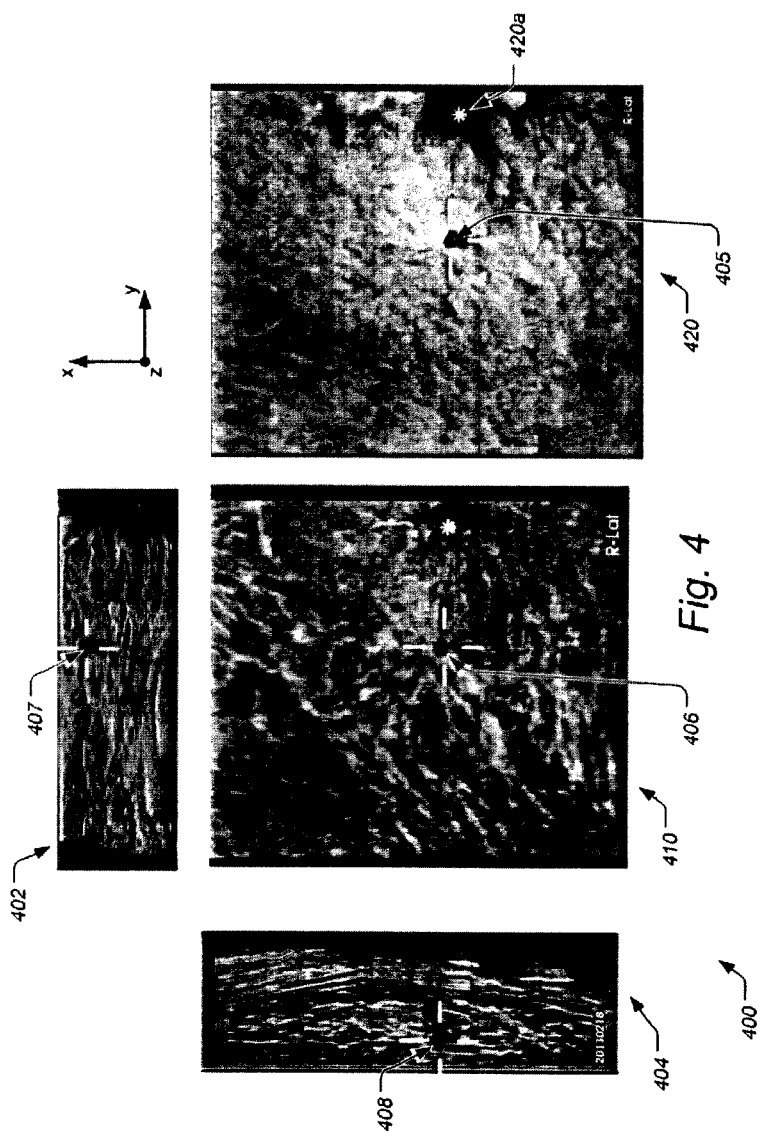
FIG. 4 illustrates aspects of a displayed whole-breast navigator overview image, an original 2D axial thin-slice image, an orthogonal 2D thin-slice image, and a coronal thick-slice image, according to some embodiments.

FIGS. 3 and 4 illustrate examples of screen displays that can make ultrasound a more practical modality for breast screening as well as diagnosis by reducing the time to identify and assess breast abnormalities and also by reducing oversight, i.e., failure to detect lesions, and can also help avoid misidentifying normal tissue as lesions.

FIG. 3 illustrates aspects of a startup screen with four enhanced, whole-breast navigator overview images, according to some embodiments. The startup screen 300 can be shown on the display of workstation 110 after a patient is scanned by an automated 3D ultrasound breast system. Startup screen 300 shows enhanced, whole-breast navigator overview images 310, 312, 314 and 316, each corresponding to a respective scan. Although there could be 5 or even more scans per breast, FIG. 3 shows just 2 scans per breast for this patient. The most prominent abnormality, 305, is on the R-Lat coronal guide image 310.

In the example of FIG. 3, enhanced, whole-breast navigator overview images 310 and 312 are from respective lateral and medial scan of a right breast with an ultrasound transducer, and images 314 and 316 are from respective medial and lateral scan of a left breast. The scans can be with equipment shown in U.S. Pat. No. 7,828,733 for scanning a chestwardly compressed breast, or from a current commercially available equipment such as the system offered in the U.S. by GE Healthcare under the trade name ABUS (see http://www3.gehealthcare.com/en/Products/Categories/Ultrasound/somo_v_ABUS_Breast_Imaging/Invenia_ABUS#tabs/tab645980A65FCD4960980BB534B4-2CFD7B). Each of the enhanced, whole-breast navigator overview images includes a star-shaped nipple mark identifying the location of the nipple, which can be added to the image by a user pointing to the nipple or from CAD identification of the nipple location. The navigator overview images are two-dimensional projections of breast tissue that was scanned with an ultrasound transducer. As noted above, content of the sonographic response due to non-breast tissue can be removed (segmented out). An important aspect of this operation is that the resulting navigator overview images and possibly other images become significantly clearer and more useful. Image 310 also shows a likely abnormality 305. This patent specification describes how to obtain such enhanced, whole-breast navigator overview images in figures and text throughout this patent specification.

FIG. 4 illustrates an example of a display that the system can generate in response to a user clicking of otherwise pointing to abnormality 305 in enhanced, whole-breast navigator overview image 310 in FIG. 3 or, alternatively, can generate automatically in response to the detection of abnormality 305 through automated image analysis. The display of FIG. 4 includes an enhanced, whole-breast navigator overview image 420 with a crosshairs pointing out an abnormality 405 (which in this example can be the same as abnormality 305 in FIG. 3), and a star-like nipple mark 420a. The display also includes a thick-slice image 410, typically of a 0.5-20 mm thick breast slice as used in current commercial products, which can be automatically selected to include the same abnormality 405, which in this case can be highlighted with a crosshairs mark. The display further includes two thin-slice images that can be automatically selected, e.g., based on the xyz coordinates of abnormality. 405, to show the same abnormality. The thin-slice images are an original axial thin-slice image 402, and an orthogonal (sagittal) thin-slice image 408 that can be automatically synthesized from a 3D image of the scanned tissue. The user can look at the enhanced, whole-breast navigator overview image 420 to see if it shows the presence of any likely abnormality and, if it does, can look for confirmation or more detail at the thick-slice 410 and thin-slice images 402 and 408 that are automatically selected for the same display, and/or at any other thick-slice or thin-slice images generated from the sonographic response. The user can also take action to scroll through some or all of the thick-slice or thin-slice images. For example, if the abnormality is a likely speculated mass, the user may elect to scroll through some or all of the thick-slice and/or thin-slice images that may contain some or all of the spiculations. This patent specification encompasses embodiments in which one or more navigator overview images for each of a patient's two breasts are shown on the same display or at least concurrently, but can also encompass other display protocols.

FIG. 4 illustrates only a single enhanced, whole-breast navigator overview image and related other images. However, it can be important to display two or more enhanced, whole-breast navigator overview images, such as from both breasts of the patents, possibly together with other, related images, to assist in screening or diagnosis that may be facilitated by comparing of the two breast, such as features related to asymmetry or other differences between the images from the two breasts. In addition, or instead, two or more whole body navigator overview images and possibly related other images of the same breast can be shown, such as concurrently or by alternating the display, such as images derived from the sonographic response to different scans of the same breast with an ultrasound transducer, from the same patient study or from patient studies taken at different times or for different breasts. Superposition of images, with or without varying transparency, also can assist the user, as can viewing images while controlling window and level of the displayed pixel values, and/or scrolling through image stacks.

In screen 400 the enhanced, whole-breast navigator overview image 420 is shown with abnormality 405 that according to some embodiments is identical to the guide image 310 and abnormality 305 shown in FIG. 3. Since the xyz coordinates have been previously computed, a click on or other identification of 405 (or 305 in FIG. 3A) immediately and automatically brings up the corresponding abnormality 406 in coronal thick-slice image 410. Also automatically displayed are the corresponding abnormalities 407 in the axial image 402 and 408 in the orthogonal image 404. The X-direction is the axial direction, which is usually parallel to the patient's head-to-toe direction, and is also typically the direction of the linear ultrasound scanning. The Y-direction is typically parallel to the patient's left-right direction. Z-direction is the chestward direction. The user who reads the images for screening or diagnosis, in most cases a radiologist, can quickly review the 2D axial scan images by activating a scroll bar in the display and scroll through the axial images. Likewise, the orthogonal images can be reviewed quickly by activating a corresponding scroll bar. The user can also elect to scroll through the thick-slice images. A whole-body navigator overview image of other image in the display of FIG. 4 that does not show abnormalities or crosshairs can mean the absence of any significant or prominent abnormalities found in the associated 3D breast volume.

Figure 5:
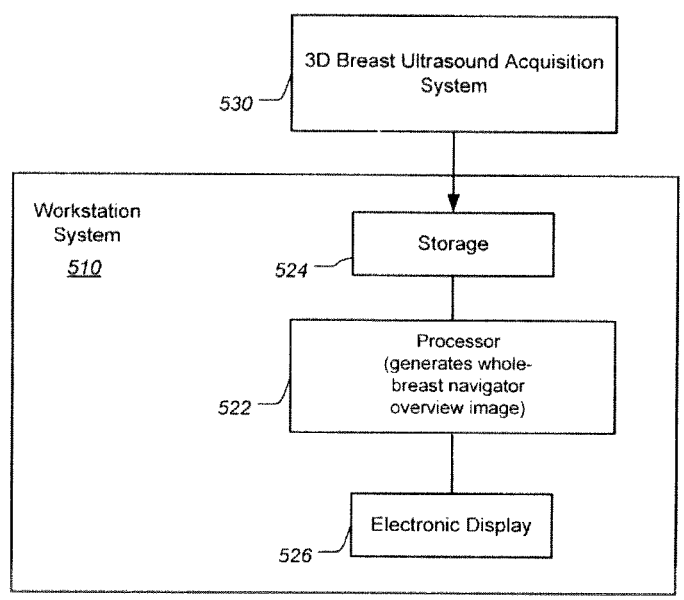
FIG. 5 is a diagram illustrating aspects of a system for generating and displaying a whole-breast navigator overview image, according to some embodiments.

FIG. 5 is a diagram illustrating aspects of a system for generating and displaying an enhanced, whole-breast navigator overview image, according to some embodiments. Block diagram 500 includes a workstation system 510 for the storage of data and processing to generate display of the navigator overview image for the reading/interpreting of the 3D breast ultrasound images. Workstation 510, which can be same as or similar to workstation 110 in FIG. 1, includes storage 524, processor 522 for generating whole-breast navigator overview images, and a display 526. Also shown is a 3-D breast ultrasound acquisition system 530 as the source of 3-D ultrasound data.

Figure 6:
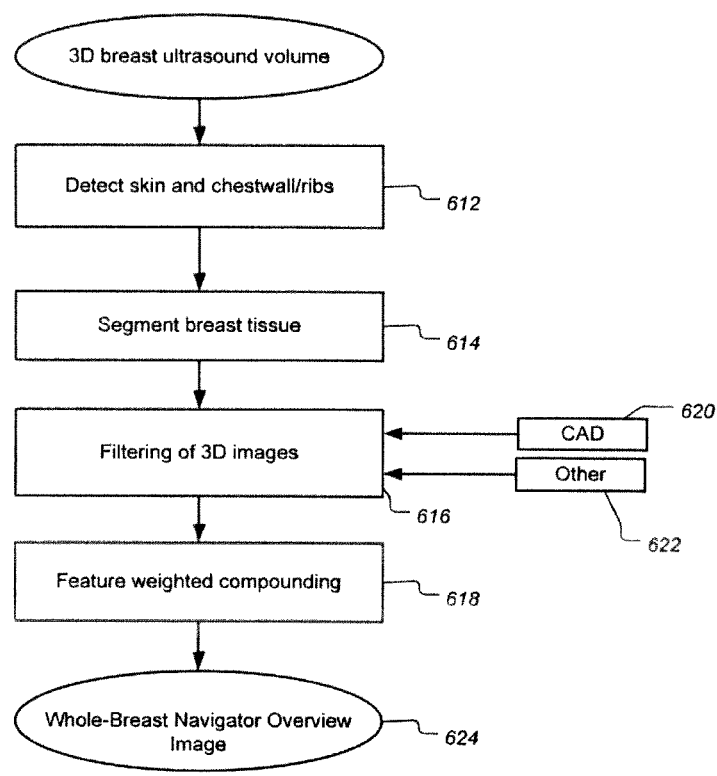
FIG. 6 is a flow chart illustrating aspects of generating and displaying a whole-breast navigator overview image, according to some embodiments.

FIG. 6 is a flow chart illustrating aspects of generating and displaying an enhanced, whole-breast navigator overview image, according to some embodiments. First, in block 612, some or all of the skin, chest-wall and ribs are detected. In block 614, the region containing only or at least mostly breast tissue is segmented. The skin region can be simply defined as the region within a certain distance range from the top or from the scanning ultrasound transducer, say 0 to 2 mm. In the Filtering block 616, the 3D volume image resulting from the sonographic response to the ultrasound energy that the transducer sent into the patient's tissue is filtered by a group of filters that are configured to suppress noise and artifacts and enhance lesions. According to some embodiments, the filters can be a gradient conversion filter and a line conversion filter. The gradient conversion filter is configured to enhance the dark rounded shapes and the line conversion filter is configured to enhance lines radiating from a center that resemble a spiculation or architectural distortion. According to some other embodiments, the filter can include a computer aided detection (CAD) algorithm 620 that detects and ranks the lesions by likelihood. Other filters 622 can be derived from techniques such as minimum voxel value, Doppler data, and/or elastography data.

In block 618, feature weighted compounding is carried out. According to some embodiments, the weights, w(x,y,z) for compounding are generated by combining the outputs of the filters:

$$w(x, y, z) = \sum_{i}^{N} k_i f_i(x, y, z)$$

where N is the total number of filters, $f_i(x,y,z)$ is the output of $i^{th}$ filter and $k_i$ is a constant scaling factor for $i^{th}$ filter. The weight is also normalized from 0 to 1 as the probability of a voxel overlap with a malignant lesion.

The enhanced, whole-breast navigator overview image a(x,y) (624) is generated by projecting the volumetric image along the z direction (excluding some or all of skin, chest-wall and rib regions) modulated by the weight. The equation below shows one example of the projection by taking the minimum value of the weighted intensity alone the z-axis.

$$a(x,y) = \text{MIN}_{across\ z}(I(x,y,z)(1-w(x,y,z)))$$

Where l(x,y,z) is the intensity or voxel value of the 3D ultrasound volumetric image.

Figure 7:
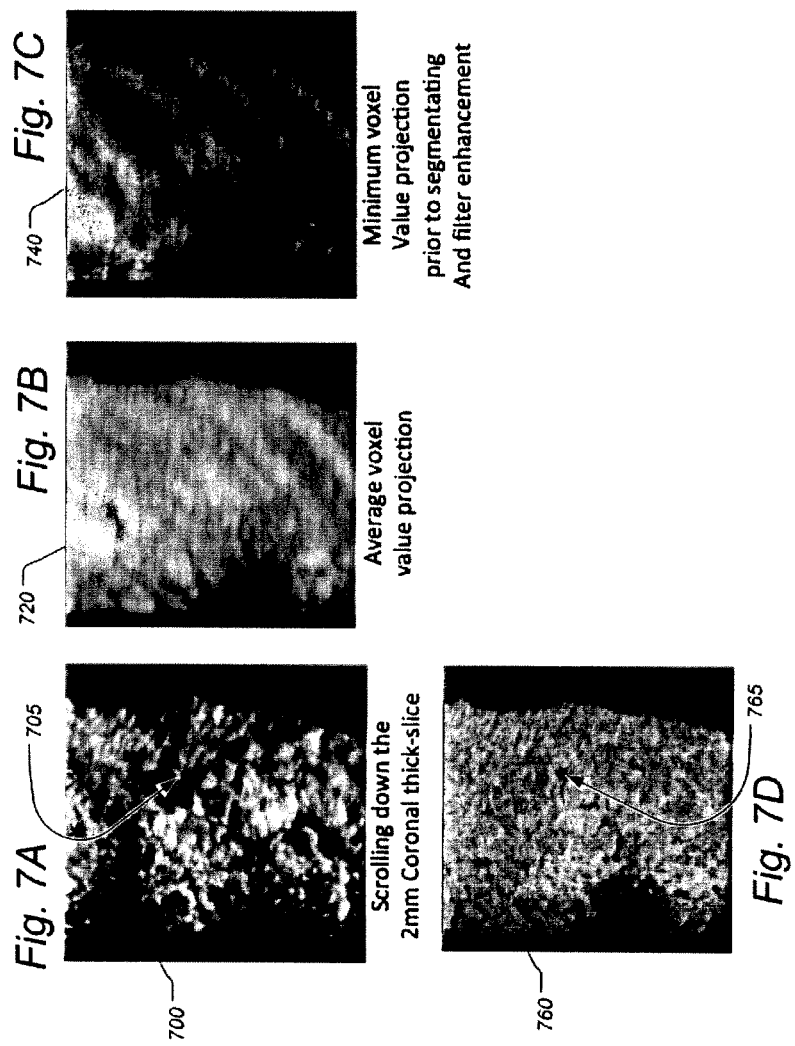
FIG. 7A-7D illustrate effects of segmenting out non-breast structures and filter enhancement of a minimum voxel value projection.

FIGS. 7A-7D illustrate effects of segmenting non-breast structures and filter enhancement of a minimum voxel value projection, according to some embodiments. A profound effect can be seen of segmentation and filter enhancement of a volumetric coronal image. FIG. 7A shows a 2 mm 2D coronal thick-slice image 700. After searching by scrolling through approximately 30 such images in the chestward (z-direction) direction, a cancer-like abnormality 705 is found. In FIG. 7B, image 720 is a 2D coronal volumetric compounding image formed by average voxel value projection. In the example of image 720, each pixel is assigned to the average voxel value along the z direction (perpendicular to the coronal image plane and chestwall) of the breast. Note that the cancer-like abnormality does not appear to be visible in image 720. In FIG. 7C, image 740 is a similar projection along the z-direction using the minimum voxel value. Again, the cancer-like abnormality does not appear to be visible. In FIG. 7D, image 760 is the minimum voxel value volumetric projection after segmenting out non-breast tissues and application of filter enhancement, which process has been described above, according to some embodiments. Note that in FIG. 7D, the cancer-like abnormality 765 is now easily visible. This example is for a thick-slice image, but also illustrates the profound benefits from similar processing for an enhanced, whole-breast navigator overview image.

Figure 8:
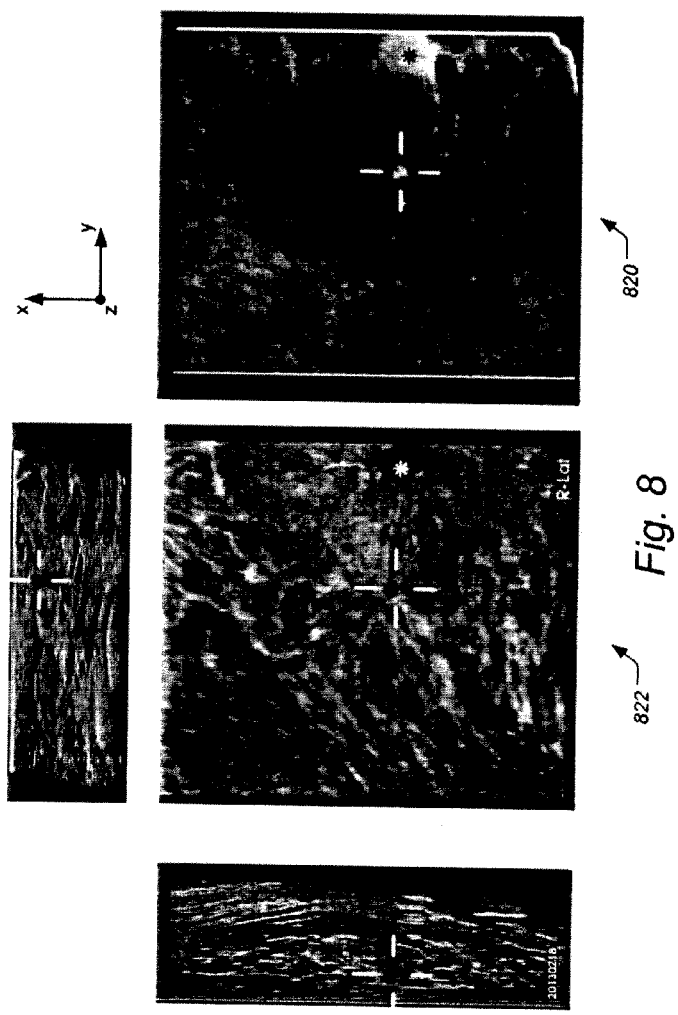
FIG. 8 illustrates aspects of a displayed inverted whole-breast navigator overview image, along with an original 2D axial thin-slice image, a synthesized orthogonal 2D thin-slice image, and a coronal thick-slice image, according to some embodiments.

FIG. 8 illustrates aspects of a displayed inverted enhanced, whole-breast navigator overview image 820 along with an original 2D axial slice 824, an orthogonal 2D slice 826, and a coronal thick-slice 822, according to some embodiments. A navigator overview image 820 is shown in reverse polarity, which some readers may find more useful.

Figure 9:
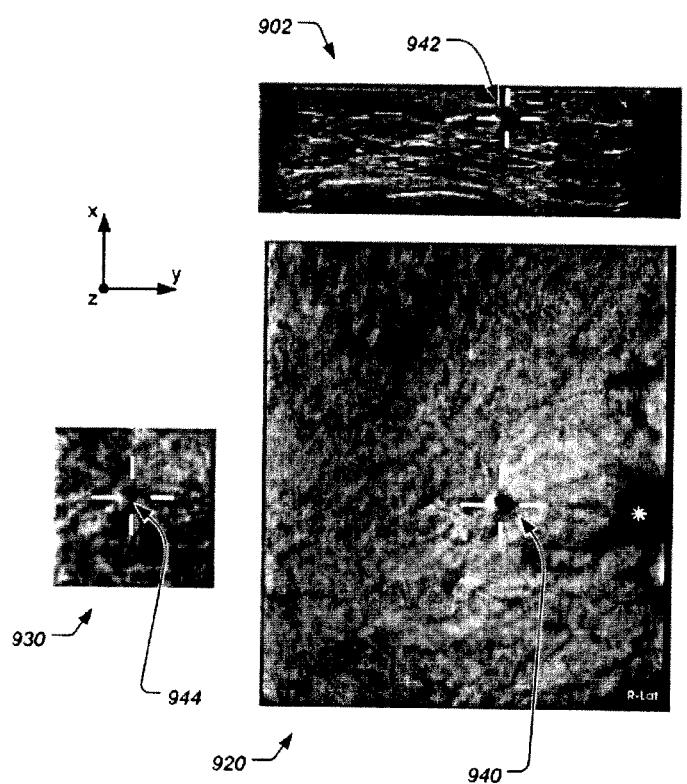
FIG. 9 illustrates aspects of a displayed whole-breast navigator overview image, along with an original 2D axial thin-slice with a snippet of a coronal thick-slice image, according to some embodiments.

FIG. 9 illustrates aspects of a displayed enhanced, whole-breast navigator overview image along with an original 2D axial slice with a snippet of a coronal thick-slice, according to some embodiments. The screen of FIG. 9 is an example with fewer display components, namely the enhanced, whole-breast navigator overview image 920, just one 2D image 902 from the scan for review and scroll review, and a snippet 930 of the 2D coronal thick-slice. According to some embodiments, instead of snippet 930, the whole 2D coronal thick-slice is displayed. The display of the 2D coronal thick-slice (or a snipped thereof) can be useful because readers can confirm their assessment by examining the presence of spiculations of the mass nodule which only show or better show in 2D composite coronal thick-slice images. Clicking the abnormality 940 in navigator overview image 920 automatically brings up the corresponding abnormalities 942 and 944 in images 902 and snippet 930, respectively.

Figure 10:
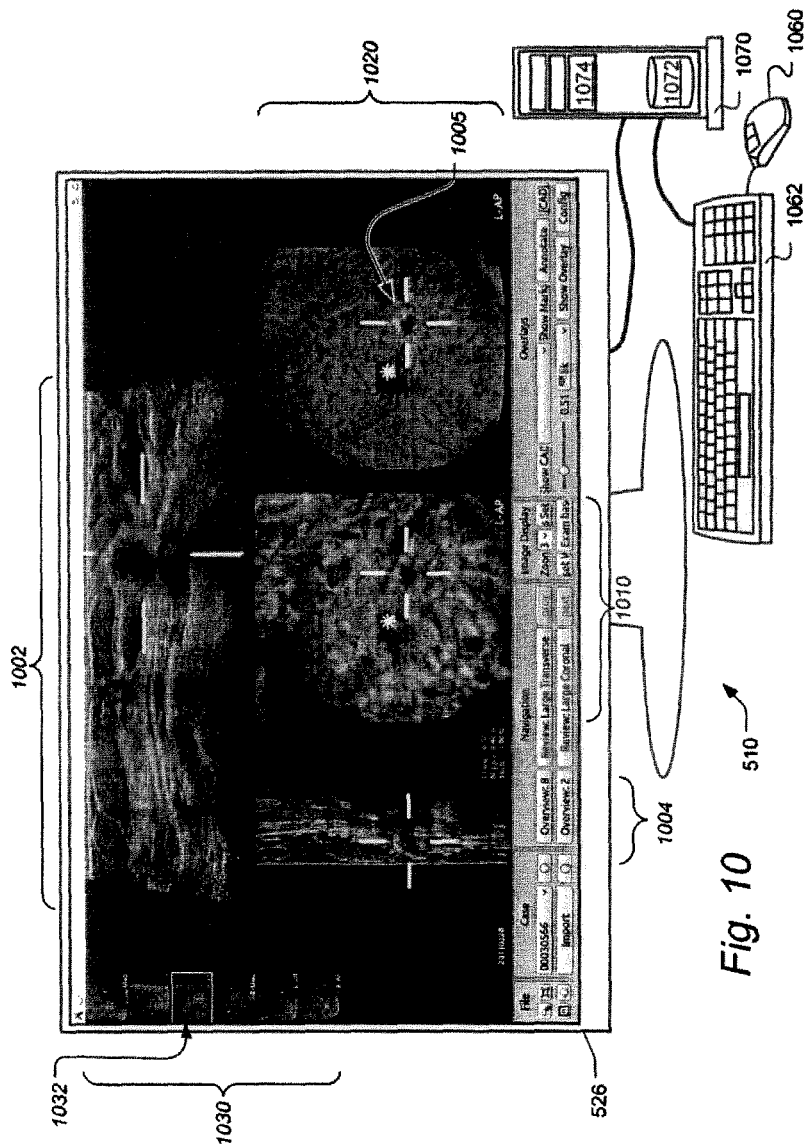
FIG. 10 shows an interactive user interface including a whole-breast navigator overview image, according to some embodiments.

FIG. 10 shows an interactive user interface including an enhanced, whole-breast navigator overview image, with an abnormality 1005, according to some embodiments. The user interface/workstation 510 includes a display 526, input devices such as keyboard 1062 and mouse 1060, and a processing system 1070. According to some embodiments, other user input methods such as touch sensitive screens can be used. According to some embodiments, user interface/workstation 510 also refers to workstation and display 110 in FIG. 1A, supra.

Processing system 1070 can be a suitable personal computer or a workstation that includes one or more processing units 1074, input/output devices such as CD and/or DVD drives, internal storage 1072 such as RAM, PROM, EPROM, and magnetic tape storage media such as one or more hard disks for storing the medical images and related databases and other information, as well as graphics processors suitable to power the graphics being displayed on display 526.

In contrast to using each coronal thick slice as a "guide image" as in the conventional approaches (e.g. shown in FIG. 22), the user interface/workstation 510 includes a whole-breast navigator overview image 1020 that combines information from the whole 3-D image of breast tissue. Also in contrast to the conventional thick or entire-breast conventional images, the navigator overview images described in this specification are enhanced by segmenting out influences of non-breast tissue that can hide or obscure important abnormalities. Furthermore, in the case shown in FIG. 10, the enhanced, whole-breast navigator overview image 1020 is graphically altered to provide improved navigation pertaining to the characteristics of the lesion features to the user/physician as to which lesion(s) can or should be given priority for interpretation. More specifically, according to some embodiments, more efficient methods and systems in breast cancer detection with 3D volumetric ultrasound are provided by detecting and displaying enhanced features of suspicious lesions, and at the same time by detecting and marking the more obvious benign lesions as benign.

According to some embodiments, display screen 526 includes reduced size and resolution versions 1030 of all or at least several of the whole-breast navigator overview images of the 3D scans of both breasts of the patient, shown on the left side edge of the screen. In this example, three 3-D volumetric scans are made on each breast of the patient. The reduced resolution version 1030 includes the currently viewed image 1032 which is displayed in higher resolution and larger size as enhanced, whole-breast navigator overview image 1020. A spiculated lesion 1005, which has a high probability of being a cancer, is shown in the coronal thick-slice view 1010. Corresponding views in the original 2D scan image 1002 as well as the constructed orthogonal 2D image 1004 all show characteristics of high probability of being a cancer. According to some embodiments, the whole-breast navigator image 1020 is altered such that the spicules of the spiculated lesion 1005 can be seen prominently in enhanced, whole-breast navigator overview image 1020. This added information allows the user/physician to pay immediate attention to this feature.

Figure 11:
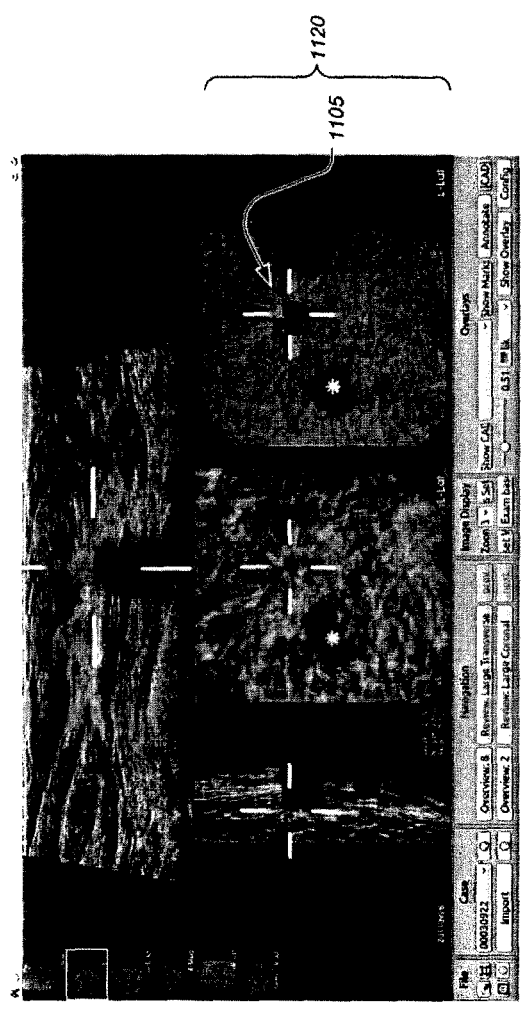
FIG. 11 shows a screen shot of an interactive user interface including another whole-breast navigator overview image, according to some embodiments.

FIG. 11 shows a screen shot of an interactive user interface including another enhanced, whole-breast navigator overview image, according to some embodiments. The screen shot 1100 of display 526 (not shown) includes a whole-breast navigator overview image 1120 with another spiculated lesion 1105. As in the case of FIG. 10, the enhanced, whole-breast navigator overview image 1120 is altered to enhance the spicules, which increases the priority of being examined further or perhaps re-checked by the user/physician.

Figure 12:
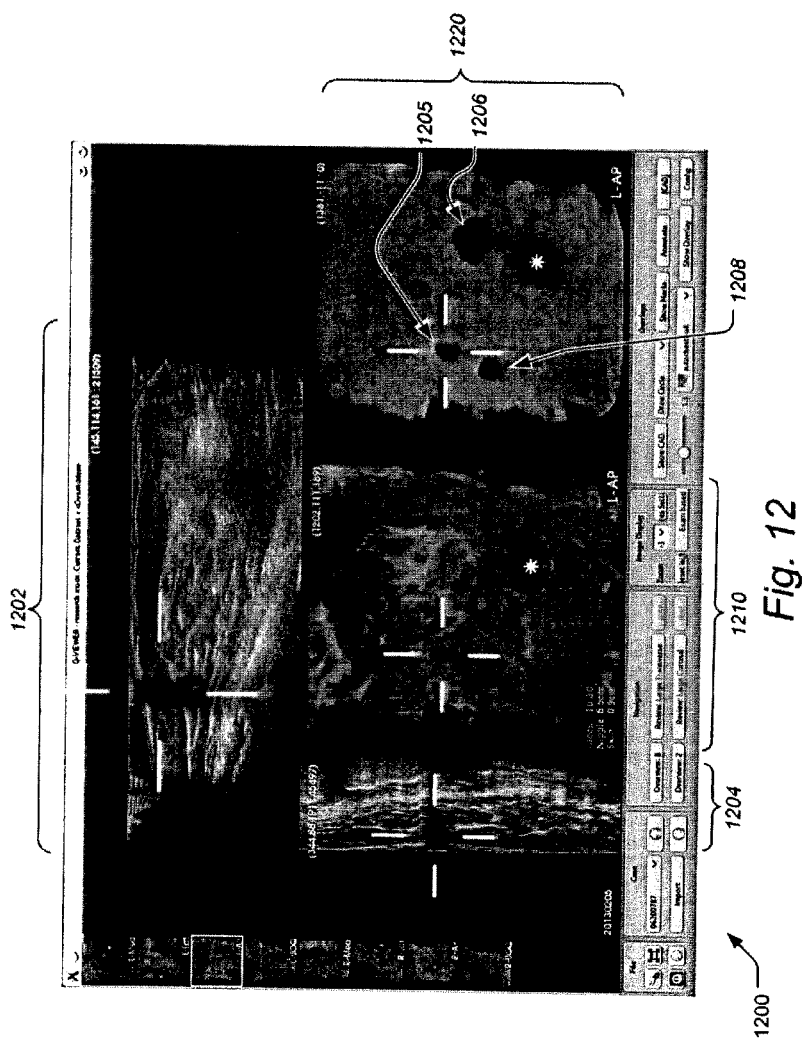
FIG. 12 shows a screen shot of an interactive user interface including an enhanced, whole-breast navigator overview image having multiple regions of interest, according to some embodiments.

FIG. 12 shows a screen shot of an interactive user interface including a two-dimensional enhanced, whole-breast navigator overview image having multiple regions of interest, according to some embodiments. In the case of image 1220, a suspicious lesion 1206 can be seen together with two prominent artifacts 1205 and 1208. Artifact 1205 is shown 4 times in this screen shot: once in the navigator overview image 1220, once in the corresponding coronal thick-slice image 1210, once in the original axial 2D scan 1202 and last in the constructed orthogonal 2D scan image 1204. From these 4 views, by clicking on or otherwise pointing to the artifact 1205 in the image 1220 to thereby bring up the other images on the display, it is quite apparent that this artifact is a "contact artifact" formed by poor acoustic coupling. However, it has been found that such artifacts can nevertheless be highly distracting to the user physician who then spends valuable time to check them. Also visible in FIG. 12 is another similar contact artifact 1208.

Figure 13:
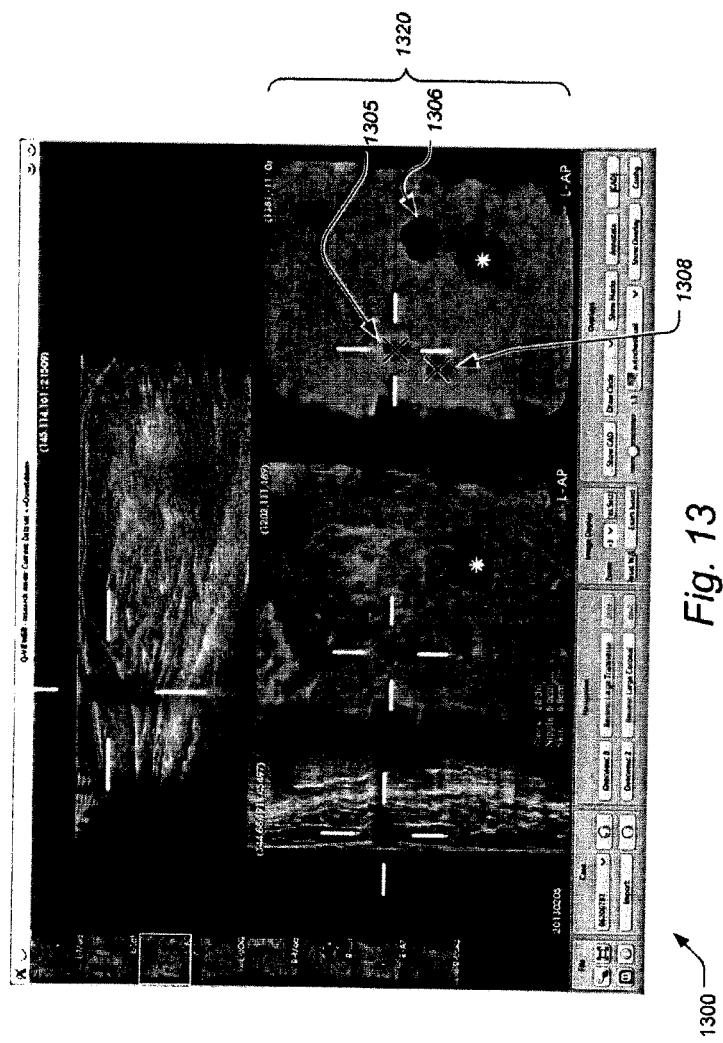
FIG. 13 shows a screen shot of an interactive user interface showing a method of graphically marking artifacts in an enhanced, whole-breast navigator overview image, according to some embodiments.

FIG. 13 shows a screen shot of an interactive user interface showing a method of graphically marking artifacts in an enhanced, whole-breast navigator overview image 1320, according to some embodiments. The screen shot 1300 is similar to the shot 1200 in FIG. 12, except that in this example the CAD software marks the artifacts 1305 and 1308 with an "x" after detecting the artifacts, according to some embodiments. In this fashion, marking the artifacts with a distinctive marker allows the user/physician to shift priority to examine the suspicious lesion 1306 first. According to some embodiments, known CAD software is used detect artifacts. By graphically marking the artifacts in the guide image, users/physicians can easily identify the artifacts and dismiss them.

Thus, the display can show not only abnormalities that are likely to be malignant but also abnormalities that are likely to be benign, and can identify them as such, e.g., crosses for likely benign or artifact abnormalities such as 1305 and 1308 in FIG. 13 but no crosses or different marks for likely malignant abnormalities such as 1105 in FIG. 11.

Figure 14:
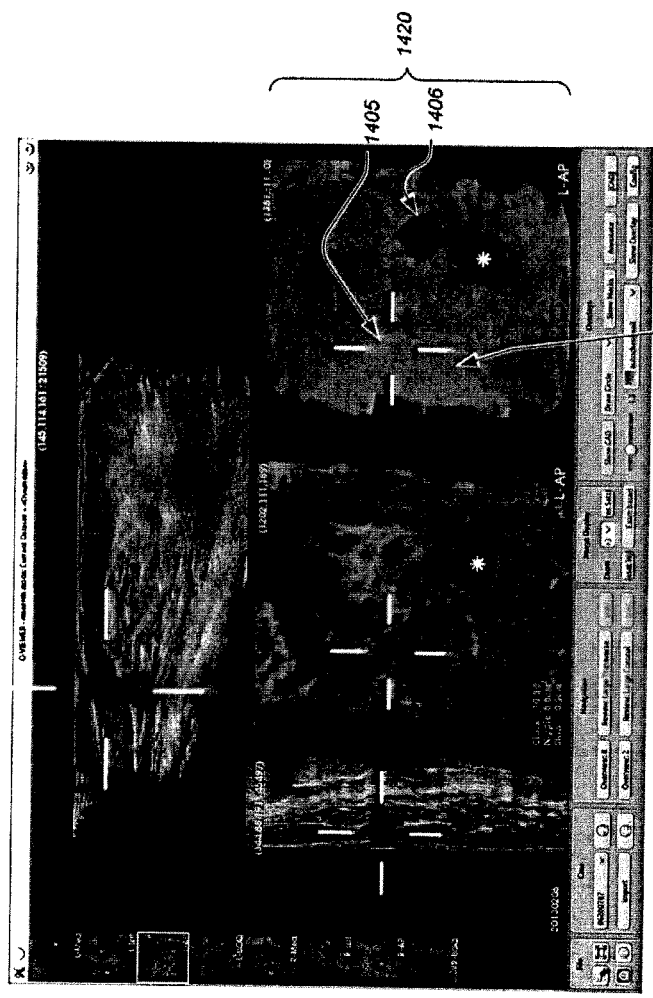
FIG. 14 is a screen shot of an interactive user interface showing another method of graphically altering artifacts in an enhanced, whole-breast navigator overview image, according to some embodiments.

FIG. 14 is a screen shot of an interactive user interface showing another method of graphically altering artifacts in an enhanced, whole-breast navigator overview image, according to some embodiments. In this example, graphical "filling in" of the detected artifacts is used to reduce the users'/physicians' attention to the artifacts. According to some embodiments, the artifacts 1405 and 1408 have been filled in the navigator overview image 1420 with background grey level. The user/physician is quickly and efficiently able to shift priority to examine the suspicious lesion 1406 first.

Figure 15:
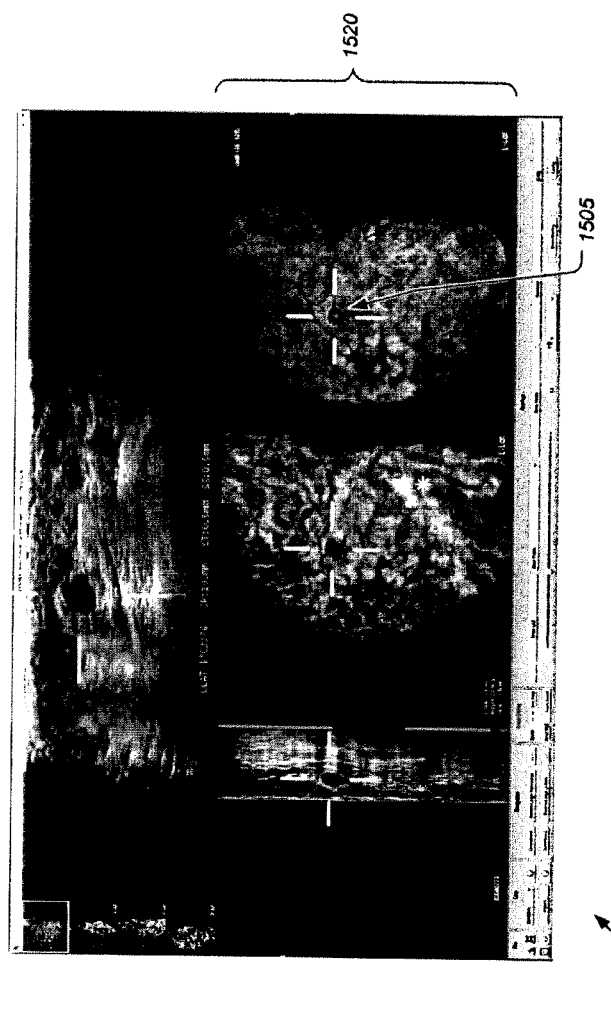
FIG. 15 is a screen shot of an interactive user interface including a graphically altered whole-breast navigator overview image showing a cyst, according to some embodiments.

FIG. 15 is a screen shot of an interactive user interface including a graphically altered enhanced, whole-breast navigator overview image showing a cyst, according to some embodiments. In whole-breast navigator overview image 1520 of screen shot 1500, a cyst 1505 is shown. In this example, the cyst 1505 is graphically marked with a white spot in the middle of the dark area, according to some embodiments.

Figure 16:
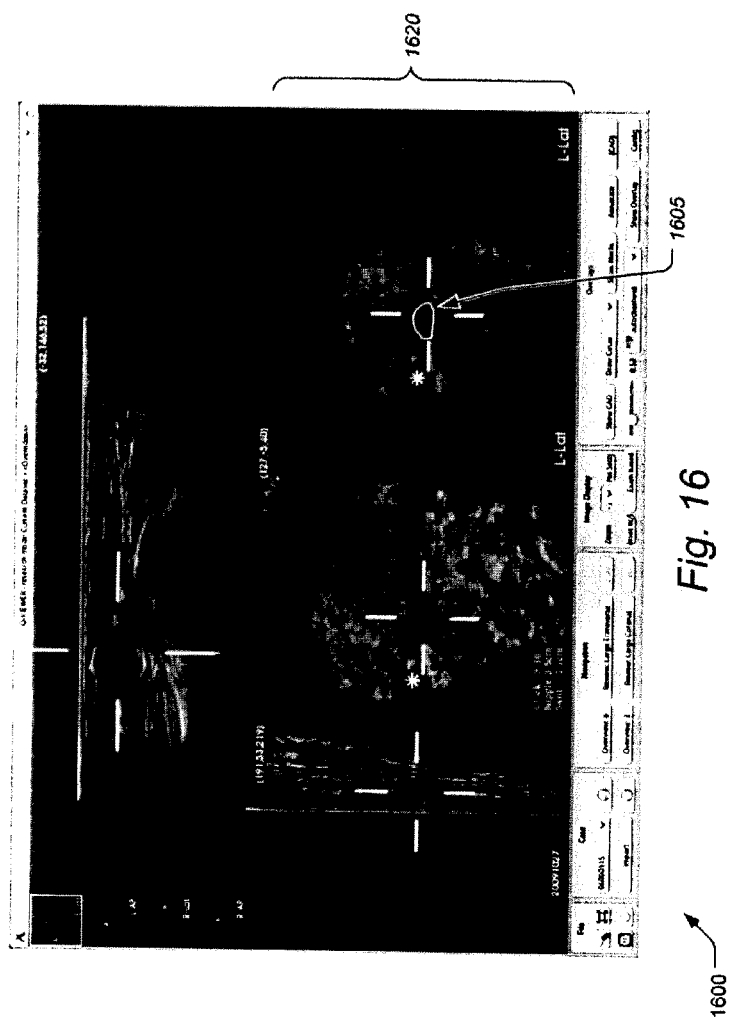
FIG. 16 is a screen shot of an interactive user interface including a graphically altered whole-breast navigator overview image showing a fibroadenoma, according to some embodiments.

FIG. 16 is a screen shot of an interactive user interface including a graphically altered enhanced, whole-breast navigator overview image showing a fibroadenoma, according to some embodiments. In whole-breast navigator overview image 1620 of screen shot 1600, a fibroadenoma 1605 is marked with a white border around the dark area, according to some embodiments.

Figure 17A:
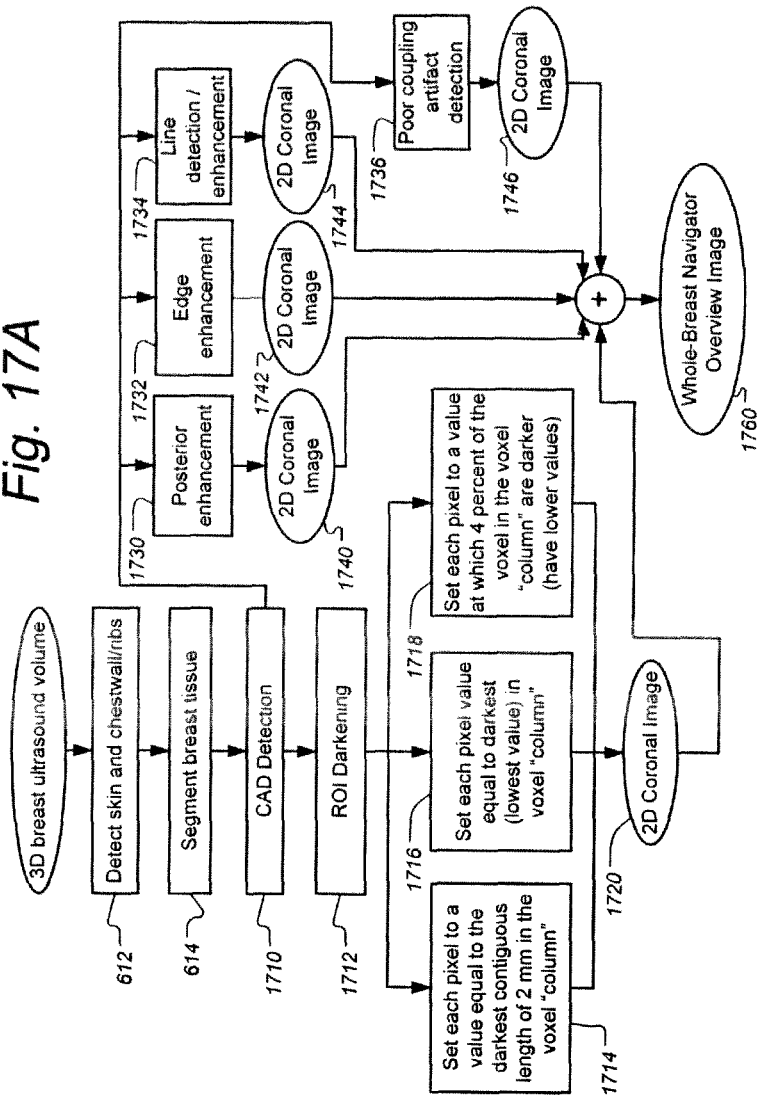
FIG. 17A is a flow chart illustrating aspects of generating an enhanced, whole-breast navigator overview image based on 3-D image data using CAD, according to some embodiments.

FIG. 17A is a flow chart illustrating aspects of generating an enhanced, whole-breast navigator overview image based on 3-D image data using CAD, according to some embodiments. Blocks 612 and 614 are similar or identical to those shown and described with respect to FIG. 6, supra. In block 1710, CAD is used to detect regions of interest (ROIs). Note that for diagnostic procedures, users/physicians have been using 2D ultrasound to distinguish and classify breast lesions for some time. For example, see the study by Stavros et al. in 1995 Radiology, Vol. 196, pages 123-134, entitled: "Solid breast nodules: Use of sonography to distinguish between benign and malignant lesions". CAD algorithms have been developed to distinguish between benign and malignant lesions in 2D and 3D images. For example, see (a) the study by Drukker et al. in 2002 Medical Physics, Vol. 29, pages 1438-1446, entitled: "Computerized lesion detection on breast ultrasound"; and (b) the study by Tan et al. in 2012 IEEE Trans. on Med. Imaging, Vol. 31, pages 1034-1042, entitled: "Computer-aided lesion diagnosis in automated 3D breast ultrasound using coronal spiculation". For screening purposes, most, if not all, of the prior CAD developments have been concentrated on detecting malignant lesions. However, according to some embodiments in block 1710, a CAD algorithm can be used to detect likely malignant lesions as well as likely benign lesions. A primary reason for detecting benign lesions and marking them in 3D volumetric ultrasound is to lower the distraction by these likely benign lesions during the interpretation by users/physicians in screening procedures. For further examples of CAD and computer-aided classification, see, e.g. Karen Drukker, et. al., "Computerized Detection Of Breast Cancer On Automated Breast Ultrasound Imaging Of Women With Dense Breasts," Med. Phys. 41 (1), pp. 012901-1-9, January 2014; Tao Tan, et. al., "Computer-aided Detection of Cancer in Automated 3D Breast Ultrasound," IEEE Transactions On Medical Imaging, pp. 1-10; Tao Tan, et. al., "Computer-Aided Lesion Diagnosis in Automated 3-D Breast Ultrasound Using Coronal Spiculation," IEEE Transactions On Medical Imaging, Vol. 31, No. 5, pp. 1034-1042, May 2012; and Woo Kyung Moon, et. al., "Computer-Aided Classification Of Breast Masses Using Speckle Features Of Automated Breast Ultrasound Images," Med. Phys. 39 (10), pp. 6465-6473, October 2012. One of more of the CAD algorithms in the cited publications can be used in step 1710, by suitably configuring ultrasound engine 106 and or workstation 110 in FIG. 1 by software, firmware; and/or hardware, as can be appreciated by persons skilled in the technology.

Following CAD detection of ROIs, according to some embodiments, the ROIs are darkened in block 1712, for example by scaling each voxel value within each ROI according to the likelihood of malignancy as determined by the CAD in block 1710. In one example, all voxels within an ROI having a 70% chance of malignancy as determined by the CAD algorithm, are multiplied by 0.3 (1=likelihood of malignancy) which will darken the pertinent voxel values in the ROI. According to other embodiments, other methods of ROI-weighted voxel darkening can be used.

According to some other embodiments, in block 1712, the ultrasound volume data is split into low and high frequency components and a volume is produced that is a weighted combination of the low-pass (background) and high-pass (signal) components. According to some embodiments, this is accomplished by producing a background volume with any of a number of known techniques (including nonlinear smoothing, in which case the background image isn't strictly "low-pass" in the traditional sense) and deriving the signal volume as the difference between the original and the background. The simple summation of these derived background and signal volumes reproduces the original data faithfully. Over most of the volume, the two components are summed with equal weight, but in the neighborhood of a CAD ROI, the signal component is weighted more heavily, emphasizing image detail in that area.

Figure 20:
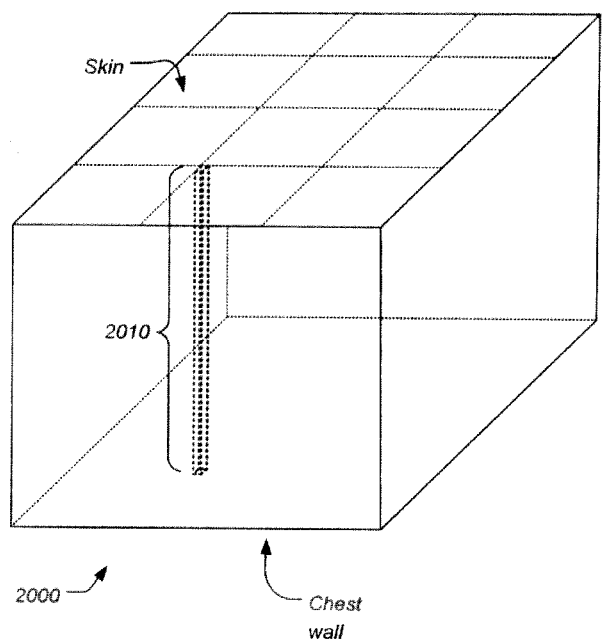
FIG. 20 is a diagram illustrating aspects of assigning 2-D pixel values based on 3-D voxel column characteristics, according to some embodiments.

After each ROI is darkened, a suitable method is used to select the appropriate pixel values for the 2-D image, such that the user's attention can be directed to the appropriate features from the 3-D image data. FIG. 20 is a diagram illustrating aspects of assigning 2-D pixel values based on 3-D voxel column characteristics, according to some embodiments. In FIG. 20, the 3-D segmented volume 2000 is depicted. One voxel column 2010 is shown. According to some embodiments, the 2-D pixel value can simply be selected by assigning it to the minimum value found in the voxel column. This option is shown in block 1716 of FIG. 17A. However, it has been found that such an approach in many cases leads to an overly noisy 2-D image that is not as useful in facilitating the user's efficient screening. It has been found that better results can often be obtained by assigning the pixel in the 2-D image to a value that is not the lowest (darkest) in the voxel column. In block 1714, the voxel column is searched for the darkest contiguous length of a specified extent, such as 2 mm, and the 2D pixel value is assigned to an average value of those contiguous voxels. Other lengths besides 2 mm can be used depending on the situation. According to some other embodiments, the pixel value is assigned to a value at which 4 percent of the voxels have lower (darker) values. Other amounts besides 4 percent can be used also, depending on the situation. According to some other embodiments, some other method of assigning 2D pixel value is used based on the voxel values. Following a suitable projection method (e.g. 1714, 1716, 1718 or some other method), a 2-D coronal image 1720 is generated.

Figure 21:
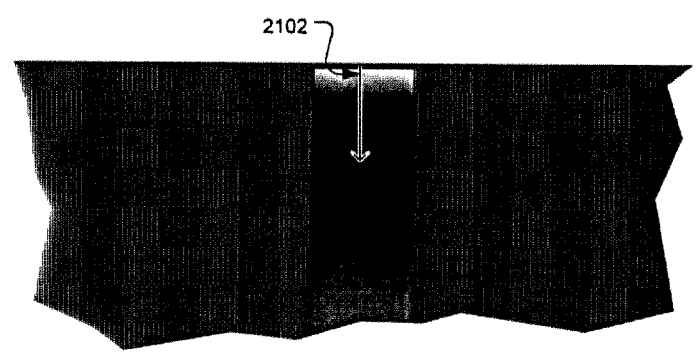
FIG. 21 is a diagram illustrating aspects of a technique for detecting poor coupling artifacts, according to some embodiments.

According to some embodiments, one or more graphical alteration techniques are also used to further enhance the usability of the resulting image. Examples of such techniques include posterior enhancement 1730, edge enhancement 1732, line detection/enhancement 1734 and poor coupling artifact detection 1736. The techniques 1730, 1732, 1734 and 1736 generate new 2-D coronal images 1740, 1742, 1744 and 1746 respectively. Posterior enhancement block 1730, according to some embodiments, adds pixel values from an area below the detected ROI, which tends to make malignant lesions darker in the center, but make benign cysts lighter in center. In block 1732, according to some embodiments, a high pass filter is used to enhance edges of ROI. In some examples, the negative values are clipped to zero and then the filtered results are added back to image. In block 1734, according to some embodiments, a line detection/enhancement technique is carried out in a volume including and above detected lesion. Techniques 1730, 1732 and 1734 are described in further detail in FIGS. 18A, 18B, 19A and 19B, infra. In block 1736, a technique is used to detect artifacts resulting from poor acoustic coupling. FIG. 21 is a diagram illustrating aspects of a technique for detecting poor coupling artifacts, according to some embodiments. In this example, an algorithm is used to detect high decreasing gradients (i.e. light-to-dark gradients) in voxel value when moving from the top (skin surface) of the 3-D image volume 2100 downwards, as indicated by the arrow 2102. The pixel value profile is calculated along the z-axis (depth). In poor acoustic contact situations, the pixel value decreases generally linearly and the slope of decrease is much steeper than in the surrounding tissue region.

Referring again to FIG. 17A, in generating the final enhanced, whole-breast navigator overview image 1760, the individual 2-D coronal images 1720, 1740, 1742, 1744 and 1746 are summed together. According to some embodiments, equal weighting can be used, but it has been found that in many cases a weighting algorithm can be more effective in generating a highly useable enhanced, whole-breast navigator overview image. In many cases it has been found that the 2-D coronal image 1720 is more heavily weighted, although the individual weights depends on which projection method (e.g. 1714, 1716 or 1718) and what types of graphical detection/enhancement techniques (e.g. 1730, 1732, 1734 and 1736) are used. The 2D coronal images 1720, 1740, 1742, 1744, and 1746 can be intermediate versions of the enhanced, whole-breast navigator overview image. Alternatively, they can be successive thick-slice images that are combined at 1760 into an enhanced, whole-breast navigator overview image.

FIG. 17B is a flow chart illustrating aspects of generating an enhanced, whole-breast navigator overview image based on 3-D image data without using CAD, according to some embodiments. FIG. 17B is similar or identical to FIG. 17A in many respects, but can be used to generate a suitable enhanced, whole-breast navigator overview image 1760 without the use of a CAD algorithm. In FIG. 17B, the skin, chest wall, and ribs are detected and segmented in blocks 612 and 614. One of the projection techniques 1714, 1716 or 1718 is then used to generate image 1720. According to some embodiments, image 1720 may be suitable for use as an enhanced, whole-breast navigator overview image 1760 without further alteration. According to some other embodiments, edge enhancement and line detection/enhancement algorithms 1730 and 1734 can be applied to the entire segmented 3-D image (rather than to just selected volumes based on a CAD ROI). According to some embodiments, the coupling artifact detection technique 1736 can be used. The resulting 2-D images are then summed together using a suitable weighting to generate the final enhanced, whole-breast navigator overview image 1760. As in the process of FIG. 17A, an alternative is to process several thick-slice images in the indicated manner and then combine then into the desired enhanced, whole-breast navigator overview image in step 1760.

Figure 18A:
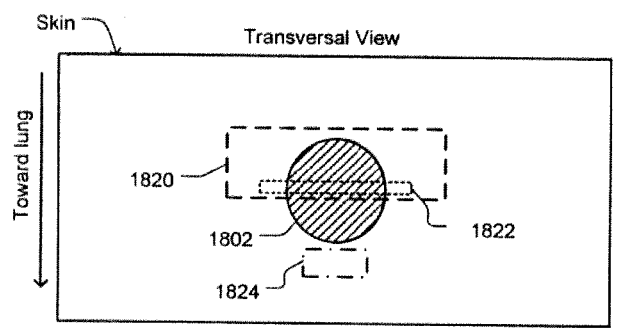
FIGS. 18A and 18B are transverse and coronal views, respectively, illustrating CAD ROI alteration techniques for use in whole-breast navigator overview images, according to some embodiments.
Figure 18B:
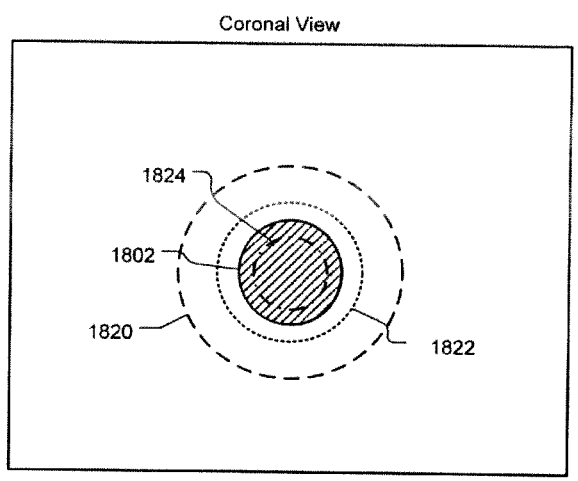

FIGS. 18A and 18B are transverse and coronal views, respectively, illustrating CAD ROI alteration techniques for use in enhanced, whole-breast navigator overview images, according to some embodiments. According to some embodiments, a line enhancement, such as second derivative of voxel filter is applied to voxels inside a sub-volume, shown as Zone 1820. The line enhancement filter is a 2D filter in the coronal plane, i.e. approximately parallel to the chest wall, where the spiculation is most prominent. The size of the sub-volume 1820 in the coronal plane is proportional to, but larger than, the size of the CAD ROI 1802 in the coronal plane. The location of the sub-volume 1820 also includes a region above the CAD ROI 1802 as seen in FIG. 18A, since this is also where spiculation is likely to be most prominent. A 2D sub-image is generated by the average voxel value of the line-enhanced sub-volume along the depth direction (skin to lung). The sub-image is then superimposed directly to the enhanced, whole-breast navigator overview image by a weighted sum of the 2-D projection of the navigator overview image and the line enhanced 2D sub-image to enhance the spiculation around the CAD ROI on the enhanced, whole-breast navigator overview.

For likely benign lesions, such as a cyst determined by CAD, the average intensity of several slices immediately behind (or beneath) the CAD ROI is calculated to compose a 2D sub-image. The size of the sub-volume in the coronal plane is proportional to, but smaller than, the 2-D size of the CAD ROI 1802 in the coronal slice, shown as Zone 1824. The sub-volume 1824 is below (or beneath) the CAD ROI 1802, such as shown in FIG. 18A. The pixel value outside the sub-image 1824 is set to zero. The sub-image is then superimposed to the enhanced, whole-breast navigator overview image by weighted sum between the sub-image and the enhanced, whole-breast navigator overview image to indicate the acoustic enhancement of a benign lesion such as a cyst. As result, a benign lesion with acoustic enhancement behind will show in the enhanced, whole-breast navigator overview image as a dark region with a white core inside as shown in FIG. 15, supra.

According to some embodiments, a high-pass, or edge enhancement filter is applied to a sub-volume 1822 around the center of the CAD ROI 1802 in the coronal slices, shown FIGS. 18A and 18B. The voxel value in the high-pass filter result sub-volume is clipped to zero if the resulting voxel value is less than zero. A 2D sub-image is generated by the average voxel value along the depth direction. The 2D sub-image is then added to the enhanced, whole-breast navigator overview image by a predetermined weight. This will create a rim around the edge of the region for a benign lesion with well-defined border, such as a fibroadenoma.

FIGS. 19A and 19B are transversal and coronal views, respectively, illustrating CAD ROI alteration techniques, according to some embodiments. The techniques described with respect to FIGS. 18A and 18B, supra (line enhancement in zone 1820, high pass filter in zone 1822 and superimposition from posterior zone 1824) can be applied to a CAD ROI simultaneously. In FIGS. 19A and 19B, three CAD ROIs 1910, 1920 and 1930 are shown. By applying the alteration techniques such as described with zones or sub-volumes 1820, 1822 and 1824 for each CAD ROI, the graphically altered result greatly facilitates distinguishing by a user. ROI 1910 is a typical cancer lesion, and is characterized by a spiculated margin, ill-defined border and no posterior acoustic enhancement. The resulting coronal view 1910 in FIG. 19B, after alteration, is shown as a dark hole with spiculated margin on the enhanced, whole-breast navigator overview image. ROI 1920 is a typical cyst, with a well-defined border, a very dark inside the lesion and a strong posterior acoustic enhancement (light shadow). After alteration, the ROI 1920 in FIG. 19B is shown as a dark hole with white rim around its border and a white core in the center of the dark hole. ROI 1930 is a typical fibroadenoma, with well-defined border, slightly dark inside the lesion and no posterior acoustic enhancement. After alteration, the ROI 1930 in FIG. 19B is shown as a slightly darker hole with a white rim around its border on the 2D guide image.

According to some other embodiments, other techniques of graphical alteration can be used to facilitate a user in quickly distinguishing malignant from benign lesions and artifacts. In one such embodiment, different colors are used. A red color, in outline, shading or both, can be used for spiculated lesions 1005 and 1105 in FIGS. 10 and 11, respectively. A green color can be used for benign lesions such as cyst 1505 in FIG. 15. According to some other embodiments non-graphical techniques can be used, such as textual or numerical markers and/or labels to further aid users in distinguishing malignant from benign lesions.

Figure 22:
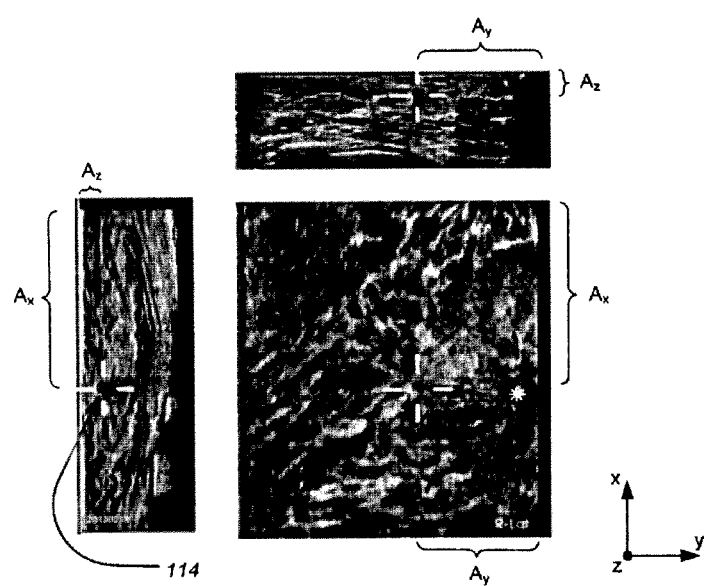
FIG. 22 illustrates the use of a thick-slice guide image, together with a thin-slice original image and a thin-slice orthogonal synthesized image, in a known commercial breast ultrasound imaging system.

FIG. 22 illustrates aspects of a known commercial system using a 2 mm thick coronal thick-slice as a road map, not an enhanced, whole-breast navigator overview image as described above in the various examples of this patent specification. Shown is a road map in the form of currently used commercial "composite coronal thick-slice" method for the reading/interpreting of the 3D breast ultrasound images. The current commercial automated 3D breast ultrasound systems typically use a thick-slice 100 having a thickness of 0.5 to 2 mm. Moving to thinner and thinner thickness with commercial systems means that readers must search through greater numbers of thick slices. For example, currently a user may have to search through 20 to 30 composite coronal thick-slices per scan, which can still be a 10× reduction of search volume vs. the raw 2D axial scan images. In the meantime, readers at hundreds of facilities may still struggle to reach the 3-minute read time limit. When viewing two dimensional ("2D") coronal thick-slice images for the 3D volumetric ultrasound, the user/physician would frequently encounter many lesions with dark area features, most of which are not cancers. Each lesion needs to be examined further by looking at the corresponding 2D original scan images and constructed orthogonal 2D images. This could be highly distracting and could lead to an increase in the total interpretation time, which, for screening procedures, is very detrimental.

Figure 23A:
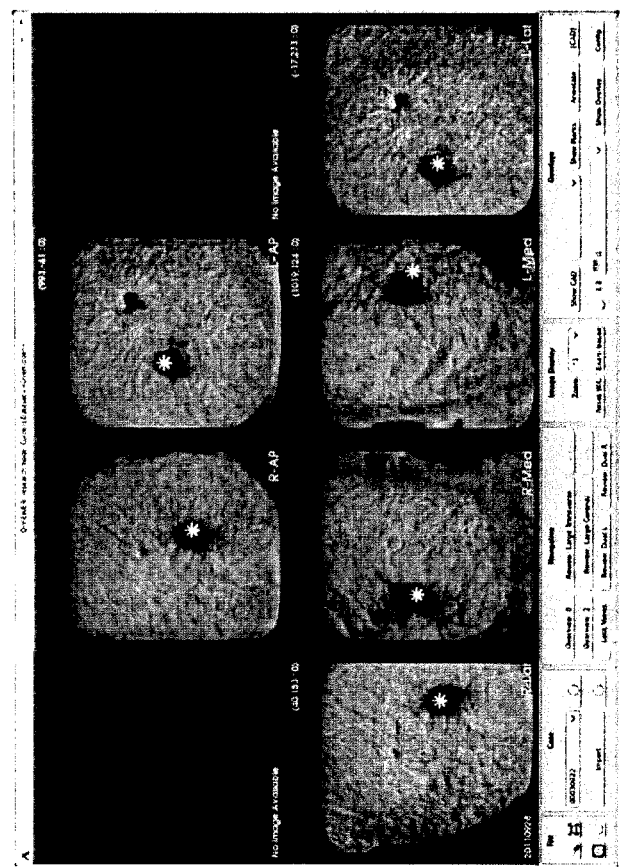
FIG. 23A illustrates another start-up display consisting of whole-breast navigator overview images, similar to FIG. 3, where the navigator images from all the scans are shown. In this case, six navigator images, three from each breast, are shown.

FIG. 23A is similar to FIG. 3 but screen 2300 illustrates three enhanced, whole-breast navigation overview images from respective AP (anterior-posterior), Lateral, and Medial scan of each of the left and right breasts of a patient, according to some embodiments. According to some embodiments, FIG. 23A is used as a typical start-up screen.

Figure 23B:
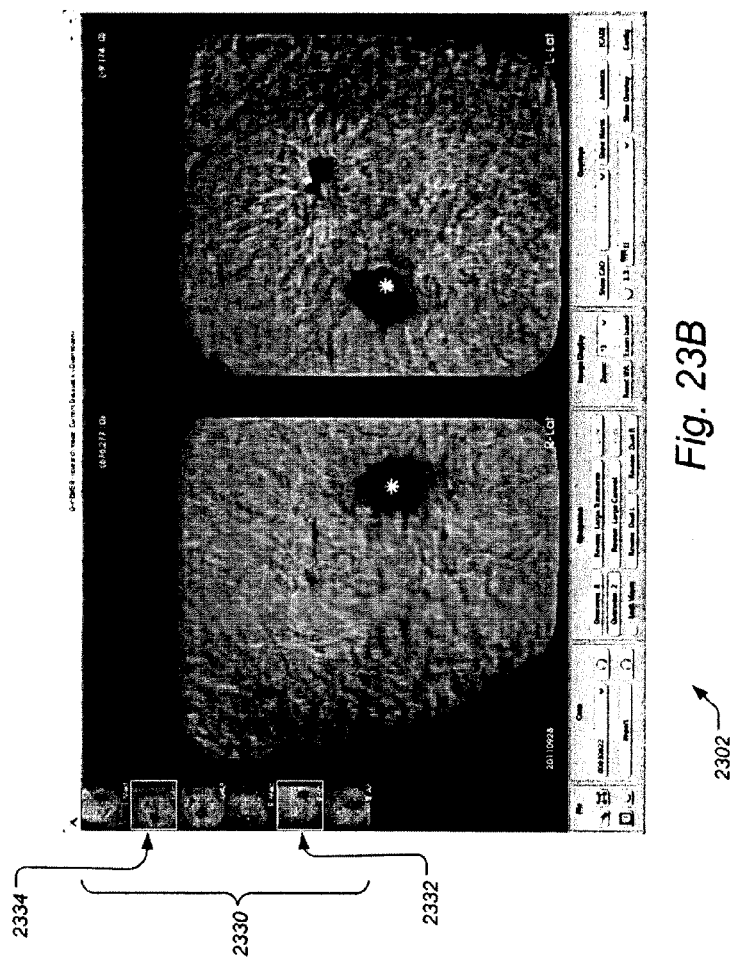
FIG. 23B illustrates yet another start-up display, similar to FIG. 23A, where a matching pair of navigators images, one from each breast, are shown side by side. This display can show the asymmetry, if any, between the right and left breasts.

FIG. 23B is similar in concept to FIGS. 3 and 23A but screen 2302 illustrates only a single pair of enhanced, whole-breast navigation overview images, one for each breast (R-Lat and L-Lat), and also shows on the left a vertical array 2330 of reduced-size versions of six available similar navigator overview images where the two (2332 and 2334) that correspond to the full-size images are boxed, according to some embodiments, which facilitates breast image comparison to help in detecting features such as asymmetry and architectural distortions.

Figure 23C:
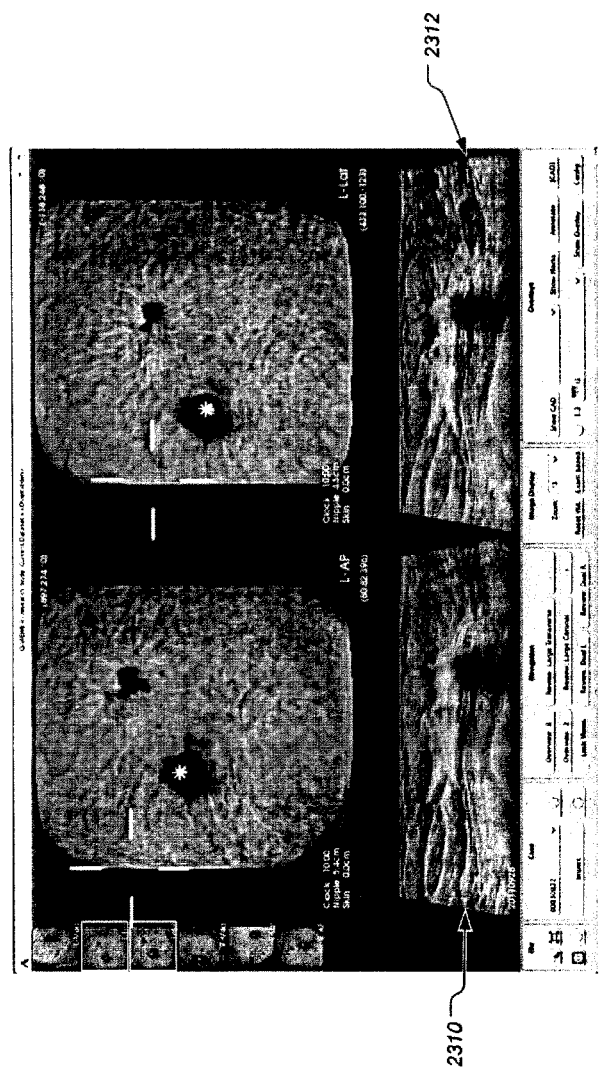
FIG. 23C illustrates yet another start-up display, similar to FIG. 23A, where two navigator images from the same breast are shown. This display shows an abnormality that shows up in more than one of the navigator images.

FIG. 23C is similar to FIG. 23B but screen 2304 adds a display of two thin-slice images 2310 and 2312 that include the abnormalities seen in the respective full-size navigator overview images, according to some embodiments. By simultaneously displaying to a user two or more whole-breast navigation images, a user can easily distinguish abnormalities which appear on more than one navigation image from scan artifacts that only show up in one navigator image.

According to another embodiment, further gains in efficiency in the reading/interpretation time can be obtained by displaying one or more auxiliary images (e.g. "pop-up" images) or by automatically switching to in-depth view screens, as will now be described. In some examples, for each discernable ROI within any whole-breast navigator overview image, a portion of the original axial thin-slice image (and portions of other images) containing the same ROI is saved. When a user's cursor (or pointer) hovers or dwells in the vicinity of the ROI in the navigator image, or the ROI is otherwise identified, the saved portion of the original axial thin-slice image (and portions of other images) is displayed next to the ROI as a "pop-up" sub-image. In one example, when the user moves the cursor away from the ROI, then the pop-up image is removed. According to some embodiments, the user can "bookmark" or save any ROI location, for example by double clicking, right clicking or similar fashion, which visually alters (e.g. highlighting) the ROI. This feature can aid the user in not accidentally having to re-evaluate an ROI. As discussed above with respect to FIGS. 10-16, a user "clicking" on or otherwise identifying a discernable ROI will bring up the 2D and thick-slice images that correspond to the ROI location. By automatically saving and displaying the "pop-up" images as described, the user can more quickly and efficiently evaluate the discernable ROIs in the navigator overview or other images.

Figure 24:
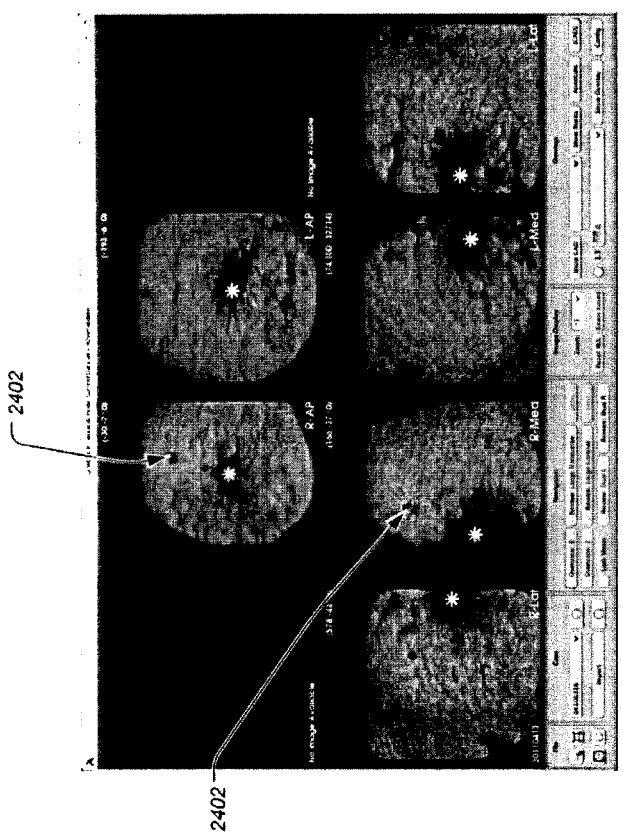
FIG. 24 illustrates yet another start-up display consisting of whole-breast navigator overview images similar to FIG. 23A.

FIG. 24 shows another typical start-up screen with enhanced, whole-breast navigator overview images of the same patient's breasts, obtained by processing the same original axial thin-slice images taken in the same sweeps of an ultrasound transducer over the same breasts. In the enhanced, whole-breast navigator overview images of FIG. 24, an abnormality 2402 with spicules is prominent in the R-AP image and the R-Med enhanced, whole-breast navigator overview images. Clicking on or otherwise identifying an abnormality such as the speculated mass 2402 seen in FIG. 24 can automatically bring up additional images relevant to the abnormality, such as a thick-slice coronal view containing the abnormality, or the coronal view plus one or both of a related original thin-slice image and a synthesized orthogonal thin-slice image, each containing the abnormality. Alternatively, another action can bring up the related view or views, such as dwelling or hovering a cursor (or pointer) on a discernable ROI in an enhanced, whole-breast navigator overview image for a specified time. This can be done by programming engine 106 and/or workstation 110 to respond to an action by automatically identifying other images that also would show the abnormality, based on information such as CAD results.

Figure 25:
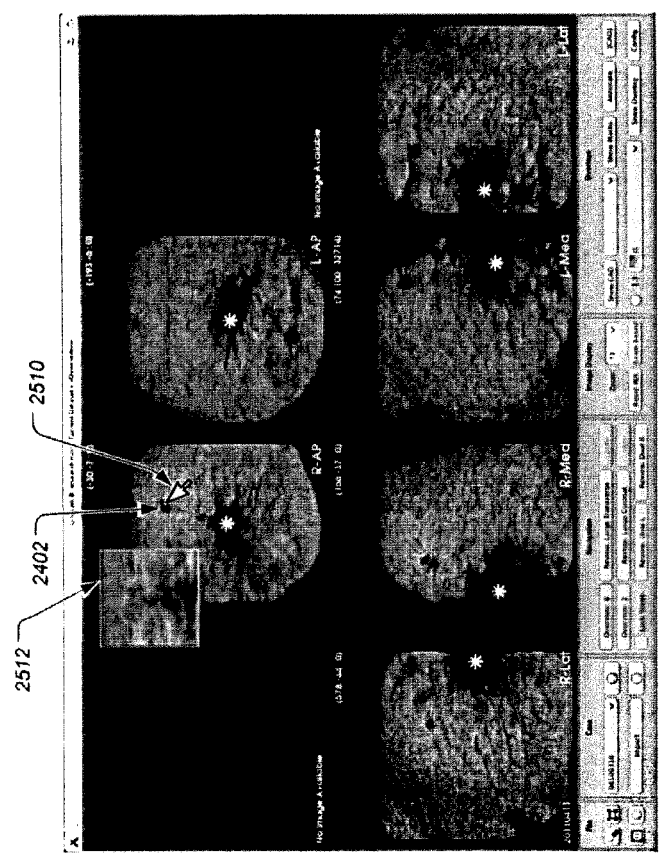
FIG. 25 is otherwise the same as FIG. 24 but adds an image of a region of interest, ROI, in an original thin-slice image, where the ROI image can appear in response to an action such as dwelling or hovering a pointer or cursor over an abnormality seen in an enhanced, whole-breast navigator overview image, according to some embodiments.

FIG. 25 illustrates the result of such cursor hovering or dwelling, according to some embodiments. In FIG. 25, the user's cursor 2510 is hovering over the prominent abnormality 2402 adds a "pop-up" image 2512 of a region of interest (ROI) from the original axial 2D thin-slice image. Because many users are familiar with evaluating original axial 2D thin-slice images, displaying a portion of the original image provides an efficient means for the user to make more accurate evaluations in the navigator images. The ROI pop-up image 2512 can appear automatically, in response to an action such as dwelling a pointer on the abnormality seen in a navigator overview image, according to some embodiments. According to some embodiments, the length of dwelling or hovering time for the user's cursor required to display the pop-up image or images can be set to a time such as 1 to 2 seconds.

Figure 26:
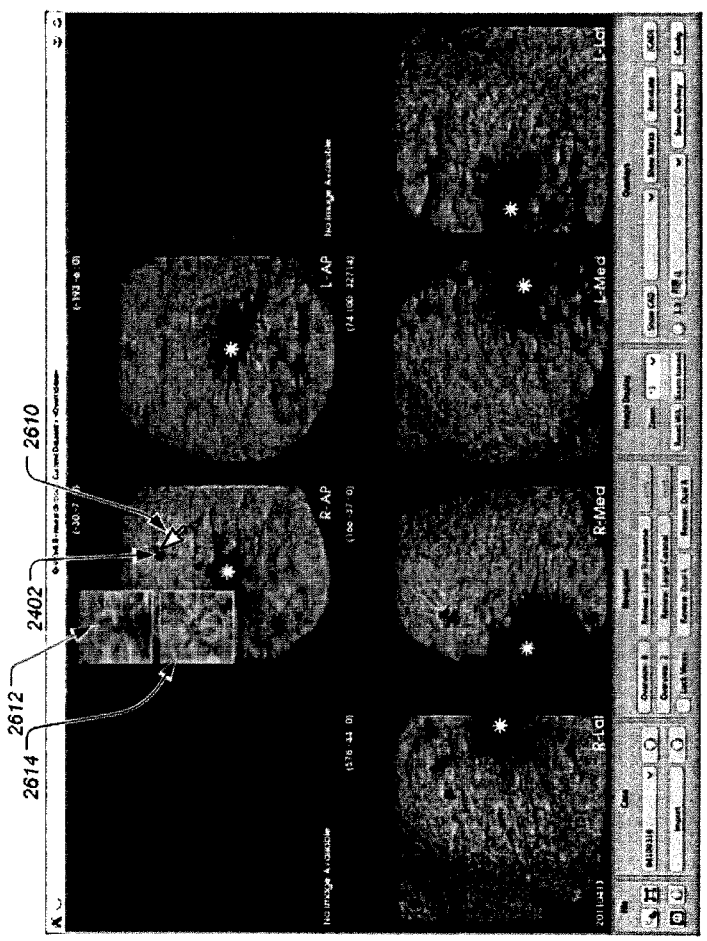
FIG. 26 illustrates an example of displaying multiple pop-up images, according to some embodiments.

FIG. 26 illustrates another examples of displaying pop-up images, according to some embodiments. In this example, the user moves a pointer such as a cursor 2610 (or a finger or some other pointer on a touch-sensitive or proximity-sensitive display) and reaches an abnormality in an enhanced, whole-breast navigator overview image, or dwells on an abnormality for some period such as 1 to 2 seconds. In response, the system automatically pops up two related ROI images 2612 and 2614. In this example, 2612 is a taken from the original axial 2D scan image, and 2614 is taken from the coronal thick-slice image. In this example, a portion of the coronal thick-slice image is provided since speculations, a major indicator of malignancy, are more visible in that image (such as in the case of pop-up image 2614). As the user moves the pointer away from that abnormality, the pop-ups automatically disappear from the screen. If the same or similar action is taken for another abnormality in an enhanced, whole-breast navigator overview image, new related pop-ups show automatically, and disappear if the pointer moves away, etc. The ROI views can help characterize the abnormality because many if not most users are familiar with thin-slice images from experience with conventional ultrasound images such as from scanning with hand-held ultrasound transducers. The addition of a related thick-slice coronal image, as in some of the disclosed embodiments, can further help in characterizing an abnormality because some features such as spicules are only seen, or are better seen, in thick-slice images. Visualization of spicules is facilitated by the chestward compression of the breast, which tends to spread the spicules along coronal planes.

Figure 27:
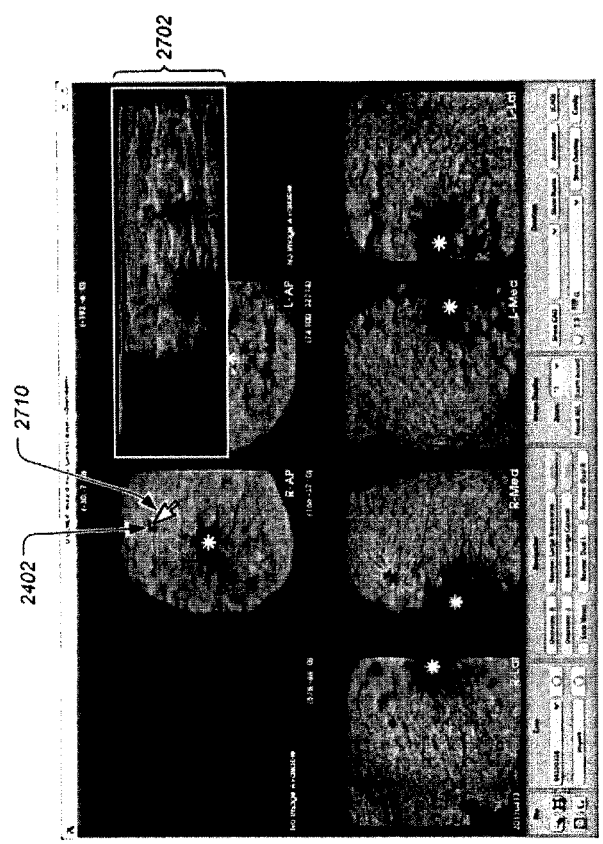
FIG. 27 illustrates automatically displaying original axial two-dimensional scan images related to a discernable region of interested selected by a user, according to some embodiments.

FIG. 27 illustrates aspects of automatically displaying an original axial two-dimensional scan image related to a discernable region of interested selected by a user, according to some embodiments. In this example, when the user hovers or dwells a cursor over a discernable ROI in a whole-breast navigation image such as ROI 2402 in FIG. 24, a full original axial 2D scan image 2702 that corresponds to the location of the ROI 2402 is displayed in an area of the screen that is either unused or used to display navigator images for the breast that does not contain the ROI in question.

Figure 28:
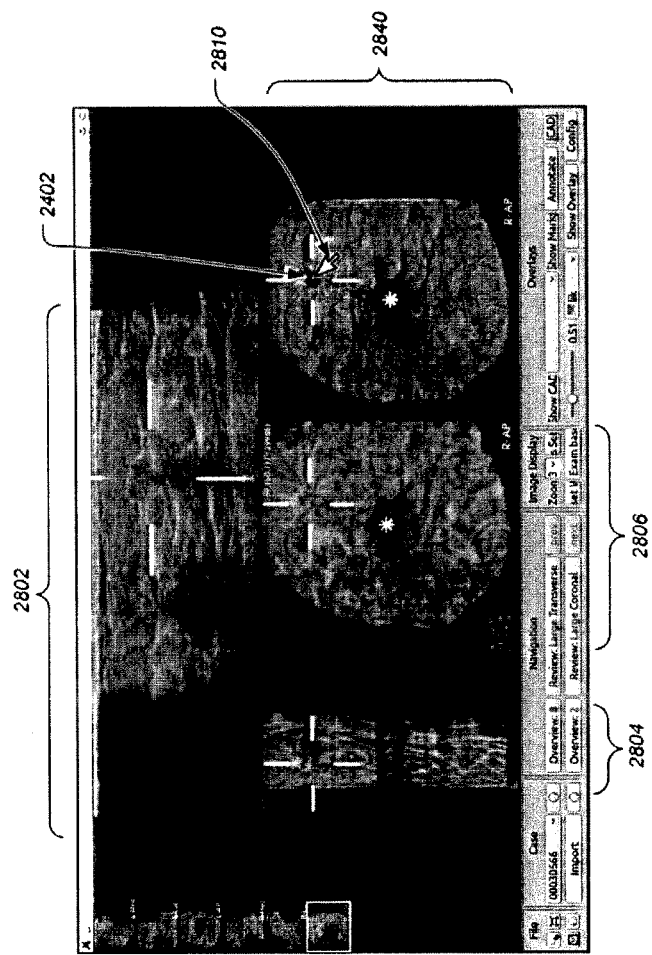
FIG. 28 illustrates automatically displaying multiple images related to a discernable region of interested selected by a user, according to some embodiments.

FIG. 28 illustrates aspects of automatically displaying multiple images related to a discernable region of interested selected by a user, according to some embodiments. In this example, when the user hovers or dwells a cursor over a discernable ROI in a whole-breast navigation image such as ROI 2402 in FIG. 24, the entire screen automatically switches to a view such as shown in FIG. 28, which includes a full original axial 2D scan image 2802, constructed orthogonal 2D image 2804, coronal thick-slice view 2804 as well as the whole-breast navigator overview image 2840. Note that the screen in FIG. 28 can be similar or identical in format to those shown in FIGS. 10-16. However, in the case of FIG. 28, the screen shown was reached in response to a user simply hovering or dwelling the cursor of the ROI 2402. Additionally, according to some embodiments, when the user moves cursor 2810 away from ROI 2402 on navigator image 2840, the screen view automatically reverts back to the view shown in FIG. 24. In this way, a user can very efficiently and effectively evaluate a discernable ROI in a whole-breast navigator image as shown in FIG. 24 by simply hovering and moving the cursor over the ROI which causes the in-depth view shown in FIG. 28. The user can then quickly return to the multi-navigator view of FIG. 24 to resume evaluation of other discernable ROIs simply by moving the cursor away from the ROI.

Figure 29:
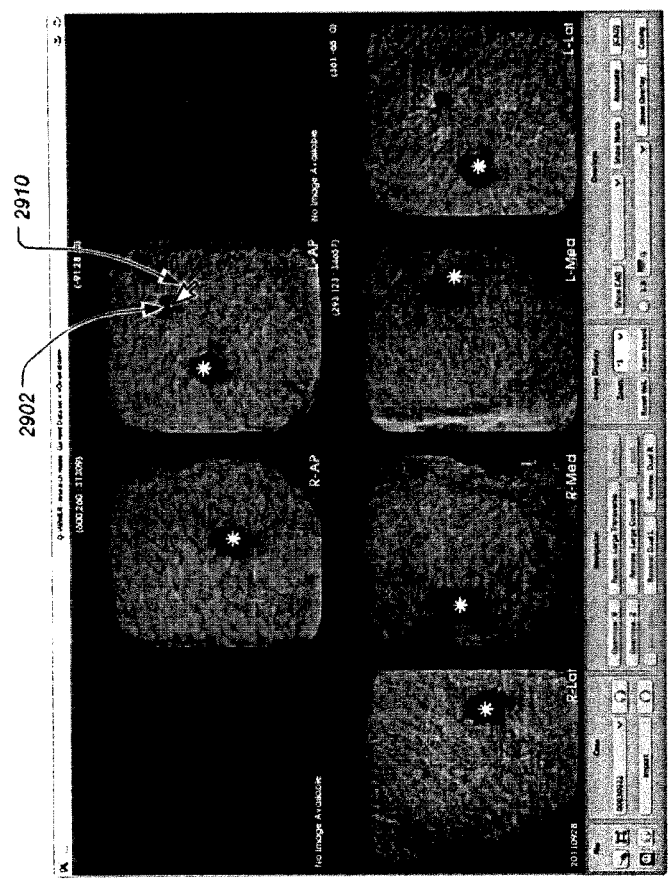
FIGS. 29 and 30 illustrate further examples of automatically displaying images related to a discernable region of interested selected by a user, according to some embodiments.
Figure 30:
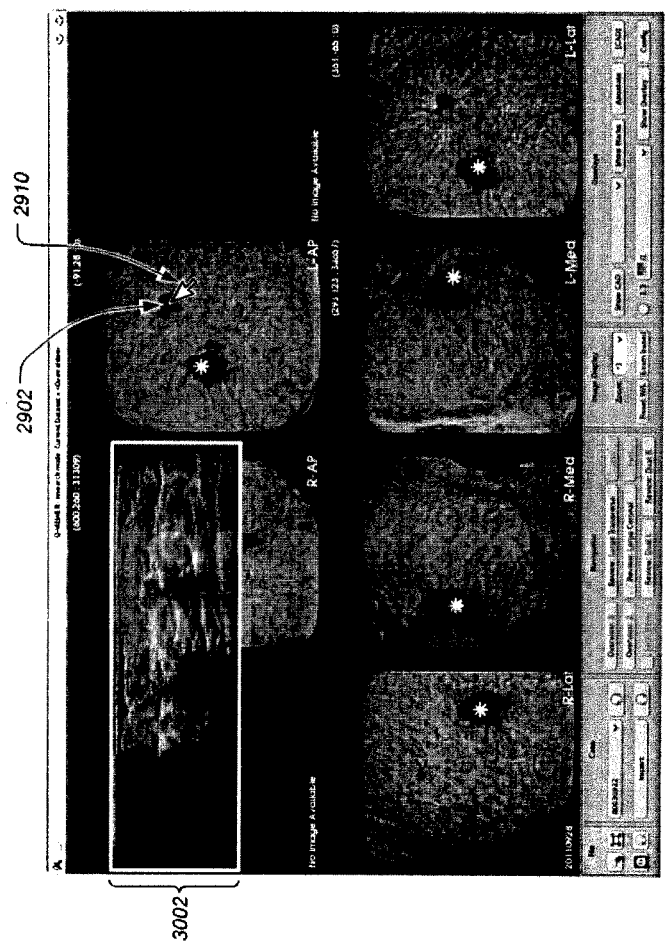

FIGS. 29 and 30 illustrate a further example of automatically displaying images related to a discernable region of interested selected by a user, according to some embodiments. In this example, a typical start up screen 2900 is shown with multiple (in this case six) whole-breast navigation overview images being displayed to a user. In this case, the user is shown positioning cursor 2910 over or near a discernable ROI 2902 in the L-AP navigator image. In response the user dwelling or hovering the cursor over the ROI 2902 for a predetermined duration (e.g. 1 to 2 seconds), the view automatically switches to screen 3000 of FIG. 30. In screen 3000, an original 2D axial scan image 3002 at a location associated with ROI 2902 is displayed. According to some embodiments, the image 3002 is displayed on the left side of the screen 3000 so as not to obstruct view of the other navigator images for the breast containing the selected ROI (in this case L-AP, L-Med and L-Lat whole breast navigator images). According to some embodiments, the user can easily choose to scroll through nearby original 2D axial scan images though a predetermined key or clicking sequence. For example, if the use right clicks while the auxiliary image window 3002 is displayed a mouse scroll wheel can then be used to page through or scroll through various 2D axial scan images in the vicinity of ROI 2902. According to some other embodiments, other key sequences can be used such as double clicking, or keyboard shortcuts, function keys, and/or arrow keys. According to some embodiments, the optional "scroll-through" or "step-though" interactive viewing of other 2-D thin slices or thick slices can also be used in connection with the screen view switching method shown in FIG. 28, or for any of the pop-up/axillary image displays shown in FIGS. 25-27.

Instead of clicking or hovering a cursor or pointer, an alternative action can initiate the appearance and disappearance of pop-ups. For example, a CAD system can identify one or more abnormalities that appear important, and can cause the display to proceed to show a pop up for the ROI of one abnormality for some period of time or until canceled by the user, then do the same for another abnormality, and so on until all abnormalities found in the navigator overview image or images have been addressed.

According to some embodiments, bookmarks are added to abnormalities after the user has had a chance to evaluate them. The bookmarks can be color, possibly indicative of the importance that the user ascribes to an abnormality, a BIRAD score, a simple mark such as a circle around an examined abnormality, and/or some other mark that can serve as a reminder of the user's work with the examined images.

Processing according to the embodiments described above can be carried out in the ultrasound engine and/or workstation equipment used in the current commercial automated breast ultrasound systems, when running programmed algorithms according to software that a skilled person can write without undue experimentation based on this patent specification and knowledge of the processing in the commercial systems. Some of the functions can be implemented using firmware or hardware instead of or in addition to software.

Various modifications may be made without departing from the spirit and scope of the new methods and systems described in this patent specification. Accordingly, the scope of this patent specification is not limited to the above-described embodiments, but instead is defined by the claims of a patent to issue thereon in light of their full scope of equivalents.

What it claimed is:

1. An automated method of screening patients including asymptotic patients with ultrasound for breast abnormalities, comprising:
   compressing down an upwardly facing breast of a supine patient with a scanning pod secured to an articulated support configured for up-down motion of the pod relative to the supine patient;

scanning the downwardly compressed breast with an electromechanically driven ultrasound transducer associated with the pod and thereby acquiring original thin-slice ultrasound images for respective up-down oriented thin-slices of the breast;

computer-processing the original thin-slice images to combine pixel values thereof into voxel values forming a 3D representation of the entire scanned 3D breast by computing the value of a voxel from the values of one or more spatially co-located pixels;

wherein said forming of the 3D representation of the entire scanned 3D breast comprises excluding breast skin and breast tissue that extends inwardly from the skin over a depth of 1-3 mm by computer-detecting a transition in at least one of the representation and the images from material outside the scanned breast and the scanned breast and determining a distance of up to 1-3 mm from the transition into the breast;

computer-comparing multi-voxel portions of the breast with surrounding multi-voxel portions of the same breast by comparing at least the shapes of the portions as defined by voxels included in the compared portions and thereby identifying abnormalities in the entire 3D scanned breast from comparison results meeting selected criteria;

computer-projecting voxel values of up-down oriented columns of voxels of the 3D representation of the entire 3D scanned breast onto respective pixels of a coronal surface through the breast that is oriented transversely to the thin-slices, to thereby form a 2D navigator representation of the entire 3D scanned breast;

said 2D navigator representation of the entire 3D scanned breast on a coronal surface comprising an array of pixel values of breast tissue and incorporating the abnormalities identified in the 3D representation of the entire 3D scanned breast;

wherein said identifying of abnormalities comprises (i) identifying abnormalities as malignant based at least in part on a shape thereof as computer-analyzed, and increasing conspicuity thereof in the displayed 2D navigator representation by making the malignant abnormality appear lighter or darker than absent the identification thereof as malignant by computer-processing the 2D navigator representation, (ii) identifying an abnormality as a cyst based at least in part on a shape thereof, and increasing a conspicuity thereof in the displayed 2D navigator representation by making the identified cyst appear lighter or darker than absent the identification thereof as a cyst by computer-processing the 2D navigator representation, and/or (iii) identifying an abnormality as a spiculation based at least on a shape thereof, and increasing conspicuity thereof in the displayed 2D navigator representation by making the identified speculation appear lighter or darker than absent the identification thereof as a speculation by computer-processing the 2D navigator representation;

said identifying of abnormalities including identifying the location thereof in 3D and storing location information regarding the identified abnormalities in computer memory;

showing on a computer display the 2D navigator representation of the entire scanned breast; and causing a programmed computer to respond to a pointing to an abnormality in the displayed 2D navigator representation by automatically carrying out the steps of providing pop-up images through:

(a) causing the computer to select from among the original thin-slice images an original thin-slice image that contains the abnormality pointed to in the displayed 2D navigator representation, said selecting including computer-processing that makes use of the location information stored in computer memory, to thereby provide a first pop-up image; and (b) causing the computer to project onto a coronal surface through the breast the voxel values of only portions of up-down oriented columns of the voxels of the 3D image that include the abnormality, to thereby construct a coronal 2D thick-slice image that shows the abnormality and represents a coronal slice of the breast that is conforms to a surface generally parallel to the chest wall of the supine patient and is thicker than the original thin-slices, to thereby provide a second pop-up image; and displaying on a computer display the first and second pop-up images that contain the abnormality pointed to in the 2D navigator representation of the entire 3D scanned breast, concurrently with displaying the 2D navigator representation.

2. An automated method of screening patients including asymptomatic patients with ultrasound for breast abnormalities, comprising:

compressing a patient's breast chestwardly with a scanning pod associated with an articulated support on which the pod is mounted for up-down motion relative to the patient, while the breast is facing up;

scanning the compressed breast with one or more ultrasound transducers associated with the pod and driven over the breast, and thereby acquiring ultrasound measurements along each of a multiplicity of chestwardly directed surfaces traversing the breast and forming therefrom a multiplicity of original thin-slice ultrasound images each of which comprises a two-dimensional (2D) distribution of pixel values for a respective chestwardly oriented original thin-slice of the breast;

storing in computer memory and spatially aligning the thin-slice images and causing a programmed computer to compute from the pixel values thereof voxel values for respective co-located elemental volumes (voxels) of a three-dimensional (3D) distribution of the voxels in the scanned breast, thereby forming a 3D representation of the scanned breast;

comparing, with a programmed computer, the voxel values of portions of the breast with the voxel values for surrounding portions of the breast for lightness, darkness, and shape thereof to thereby identify abnormalities in the breast from comparison results meeting selected criteria;

projecting voxel values of columns of voxels of the 3D representation of the scanned breast onto respective pixels of a coronal surface through the breast that is oriented transversely to the thin-slices, to thereby form a 2D navigator representation of the entire scanned breast, which 2D navigator representation comprises an array of pixel values of breast tissue and incorporates abnormalities identified in the 3D representation of the entire scanned breast;

said 2D navigator representation of the entire scanned breast excluding, by computer detection, effects of skin and breast tissue that extends inwardly from the skin to a depth of 1-3 mm from the transition into the breast;

showing on a computer display the 2D navigator representation of the entire scanned breast;

said showing comprising increased conspicuity of identifies cyst, and/or speculation abnormalities by showing such abnormalities as lighter or darker spots;

storing in computer memory at least the original thin-slice images that contain identified abnormalities and 3D positions thereof; and responding to a pointing to an abnormality in the displayed 2D navigator representation by automatically carrying out the steps of:

(c) selecting from among the original thin-slice images stored in computer memory an original thin-slice image that contains the pointed to abnormality based on parameters of the pixels or voxels thereof; and (d) computer-projecting onto a coronal surface through the breast the voxel values of only portions of chestwardly oriented columns of the voxels of the 3D image that include an identified abnormality, to thereby construct a coronal 2D thick-slice image that shows the abnormality and represents a coronal slice of the breast thicker than the original thin-slices; and (e) concurrently displaying on the computer display the 2D navigator representation of the entire scanned breast together with said original thin-slice image that includes the pointed to abnormality and said 2D thick-slice image that also includes the pointed to abnormality.

3. The method of claim 2 in which said comparing of voxel values comprises computer-implemented comparing of voxel values of multi-voxel portions of the 3D representation of the breast with voxel values or surrounding multi-voxel portions of the same breast to thereby identify and locate the position of an abnormality in the breast in three dimensions (3D) and to store the 3D position of the abnormality in computer memory, and said responding to a pointing to an abnormality in the 2D navigator representation comprises using said 3D position in computer memory in selecting said original thin-slice image showing the abnormality and in constructing said 2D thick-slice image showing the same abnormality.

4. The method of claim 2 in which the step of responding to pointing to an abnormality comprises automated responding to a user hovering a pointer over the abnormality in the displayed 2D navigator representation.

5. The method of claim 2 in which the step of responding to pointing to an abnormality comprises automated responding to a user pointing to abnormality in the displayed 2D navigator representation.

6. The method of claim 2 further including the computer implemented step of detecting influence of artifacts in the whole-breast navigator representation by comparing pixel values thereof and diminishing the appearance of the detected artifacts in the displayed 2D navigator representation by making portions thereof appear lighter or darker than before the detection of the artifacts.

7. The method of claim 2 further including the computer-implemented step of identifying the identified abnormality as malignant based at least in part on a shape thereof, and increasing conspicuity thereof in the displayed 2D navigator representation by making the malignant abnormality appear lighter or darker than absent the identification thereof as malignant.

8. The method of claim 2 further including the computer-implemented step of classifying an identified abnormality as a cyst based at least in part on a shape thereof.

9. The method of claim 2 further including the computer-implemented step of classifying an identified abnormality as a spiculation based at least on a shape thereof.

10. The method of claim 2 further including the computer-implemented step of detecting artifacts due to poor ultrasound transducer-to-breast coupling by testing pixel or voxel values of breast tissue from the breast skin into the scanned breast for departures from selected ranges and reducing conspicuity of said coupling artifacts in the displayed 2D navigator representation by changing their values to values within a range consistent with surrounding tissue of the scanned breast.

11. The method of claim 2 further including carrying out the method of scanning a patient's breast on multiple women, including asymptomatic women, to screen for cancer with ultrasound.

12. An automated system transmitting ultrasound energy into and detecting ultrasound energy emitted from a patient's breast to screen patients, including asymptotic patients, comprising:

a breast scanning pod with one or more ultrasound transducers, and articulated support on which the breast scanning pod is mounted for up-down motion relative to the patient wherein the breast scanning pod is configured to compress the breast chestwardly in said motion, while the breast is facing up;

a motorized transducer driver configured to move the one or more transducers relative to the chestwardly compressed breast to thereby scan the breast with ultrasound and provide a transducer output;

an ultrasound imaging processor comprising a module configured to receive the transducer output and apply computer algorithms thereto to calculate a multiplicity of original thin-slice ultrasound images each of which comprises a two-dimensional (2D) distribution of pixel values of a respective chestwardly oriented thin slice of the breast;

the ultrasound imaging processor further comprising a module configured to apply computer algorithms to spatially align the thin-slice images and convert pixel values thereof into voxel values of voxels of a 3D distribution of elemental volumes of the breast, thereby constructing a 3D representation of the entire breast that contains representations of abnormalities present in the breast;

the ultrasound imaging processor further comprising a module configured to apply computer algorithms to project voxel values of chestwardly oriented columns of voxels of the 3D representation into pixel values for respective pixel positions in a coronal surface traversing the breast, thereby forming a projected 2D navigator representation of the entire breast, which 2D navigator representation incorporates projections of abnormalities in the entire breast and increases the conspicuity thereof by making cyst and/or speculation abnormalities lighter or darker;

the ultrasound imaging processor being configured to store in computer memory information identifying abnormalities and positions thereof in 3D, and to exclude from the 2D navigator representation effects of skin and breast tissue that extents to 1-3 mm inwardly from a transition into the breast;

an interactive computer display screen configured to display the 2D navigator representation of the entire breast and to respond to a pointing to an abnormality therein to automatically cause the ultrasound imaging processor to:

(a) access in computer memory a position of the abnormality pointed to by the user in the displayed 2D navigator representation of the entire breast and select, based on using that position, an original thin-slice image showing the abnormality; and (b) access a position of the abnormality in the 2D navigator representation and in the 3D representation and, based on using those positions, computer-project voxel values of only portions of chestwardly oriented columns of the 3D representation onto respective pixels of a coronal surface traversing the breast to thereby construct a 2D thick-slice image that represents at least a portion of a coronal slice of the breast thicker than the thin slices and showing the abnormality; and said display screen being configured to concurrently display the 2D navigator representation of the entire breast together with at least two of (i) the original thin-slices image showing the abnormality, and (ii) the thick-slice image.

13. The system of claim 12 in which the interactive computer display screen is further configured to respond to a pointing that comprises a user hovering a pointer over the displayed abnormality in the 2D navigator representation.

14. The system of claim 12 in which the interactive computer display screen is further configured to respond to a pointing that comprises a user pointing to the abnormality in the displayed 2D navigator representation.

15. The system of claim 12 in which the ultrasound imaging processor is further configured to carry out computer-implemented detecting of influences of artifacts in the 2D navigator representation by comparing pixel values thereof and diminishing the appearance of the detected artifacts in the displayed 2D navigator representation by making portions thereof appear lighter or darker than absent said diminishing.

16. The system of claim 12 in which the ultrasound imaging processor is further configured to carry out computer-implemented identifying of breast abnormalities as malignant based at least in part on a shape thereof, and to increase conspicuity thereof in the displayed 2D navigator representation by making a malignant abnormality appear lighter or darker than absent the identification thereof as malignant.

17. The system of claim 12 in which the ultrasound imaging processor is further configured to carry out computer-implemented identifying of breast abnormalities as cysts based at least in part on a shape thereof.

18. The system of claim 12 in which the ultrasound imaging processor is further configured to carry out computer-implemented identifying of breast abnormalities as a spiculations based at least on a shape thereof.

19. The system of claim 12 in which the ultrasound imaging processor is further configured to carry out computer-implemented detecting of artifacts due to poor ultrasound transducer-to-breast coupling by testing pixel or voxel values of breast tissue from the breast skin partway only into the scanned breast rather than into the entire scanned breast for departures from selected ranges and to reduce conspicuity of a detected coupling artifact in the displayed 2D navigator representation by changing pixel values thereof to values within a range consistent with surrounding tissue of the scanned breast.

20. The system of claim 12 in which the ultrasound imaging processor is further configured to carry out computer-implemented projecting to a pixel in the 2D navigator representation of voxel values of only a multi-voxel portion of a related column of voxels in the 3D representation.

21. The system of claim 12 in which the ultrasound imaging processor is configured to compare voxel values of multi-voxel portions the 3D representation of the breast with voxel values or surrounding multi-voxel portions of the same breast to thereby identify and locate the position of an abnormality in the breast in three dimensions (3D) and to store the 3D position of the abnormality in computer memory, and the interactive computer display is configured to automatically respond to said pointing to an abnormality in the 2D navigator representation to access said 3D position in computer memory for use in selecting said original thin-slice image showing the abnormality and to construct said 2D thick-slice image showing the same abnormality.

22. An ultrasound system screening patients, including asymptomatic patients, for breast abnormalities that utilizes a single two-dimensional (2D) navigator representation of the entire depth in the chestward direction of a three-dimensional (3D) scanned breast of a supine patient, comprising:

a scanner comprising an electromechanically driven ultrasound transducer configured to move up-down relative a supine patient and to scan a chestwardly compressed breast of a supine patient subjected to screening the breast for abnormalities and thereby acquire a multiplicity of original two-dimensional (2D) ultrasound images each comprising a 2D distribution of pixel values for a respective chestwardly oriented thin-slice of the breast;

an image processing computer configured to process the original 2D ultrasound images by applying computer algorithms to compute, from the pixel values thereof, voxel values for respective co-located elemental volumes (voxels) of a 3D distribution of the voxels in the scanned breast, thereby forming a 3D representation of the entire depth of the scanned breast;

said image processing computer being further configured to process the voxel values by comparing voxel values of multi-voxel portions of the breast with voxel values of surrounding multi-voxel portions of the same breast, including for shape of said portions, to thereby identify an abnormality present in the breast and to identify a position of said abnormality in the breast in 3D, said computer including computer memory and being configured to store in said memory at least the position of the abnormality in depth in the breast;

said image processing computer being further configured to form a single 2D navigator representation of the entire depth of the scanned breast, which 2D navigator representation shows the location of the abnormality in 2D but not in a dimension representing depth in the breast and increases conspicuity of cyst and/or speculation abnormalities to a lighter or darker appearance;

wherein said forming comprises projecting voxel values of only some of the voxels of each chestwardly directed column of voxels in the scanned breast onto a respective pixel position of a 2D array of pixels arranged on a coronal surface relative to the breast;

a computer display coupled with the image processing computer to receive said 2D navigator representation of the entire scanned breast and to display the 2D navigator representation; and said computer display and said image processing computer being configured to respond to a pointing to the abnormality in the displayed 2D navigator representation by automatically, through computer processing:

(a) select from among the original 2D ultrasound images an original 2D ultrasound image that contains the pointed to abnormality based at least in part on the position of the abnormality in the breast stored in computer memory; and
(b) computer-provide a 2D thick-slice projection of voxel values of at least a portion of a thick slice of the breast that is thicker than said thin slices, onto a coronal surface relative to the breast, which thick slice includes the abnormality; and
(c) concurrently with showing the 2D navigator on the computer display, display thereon said original 2D ultrasound image that includes the pointed to abnormality and said 2D thick-slice projection onto a coronal surface that also includes the pointed to abnormality.

* * * * *